US009522956B2

(12) United States Patent
Gillies et al.

(10) Patent No.: US 9,522,956 B2
(45) Date of Patent: Dec. 20, 2016

(54) COMBINATION THERAPY USING ANTI-EGFR AND ANTI-HER2 ANTIBODIES

(71) Applicant: L'Institut National De La Sante Et De La Recherche Medicale, Paris (FR)

(72) Inventors: Stephen D. Gillies, Carlisle, MA (US); David Azria, Mauguio (FR); Christel Larbouret, Montpellier (FR); André Pelegrin, Montpellier (FR)

(73) Assignee: L'Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 14/536,854

(22) Filed: Nov. 10, 2014

(65) Prior Publication Data

US 2015/0132308 A1 May 14, 2015

Related U.S. Application Data

(63) Continuation of application No. 12/086,725, filed as application No. PCT/EP2006/012133 on Dec. 15, 2006, now abandoned.

(30) Foreign Application Priority Data

Jan. 4, 2006 (EP) ................................ 06000107

(51) Int. Cl.
| | | |
|---|---|---|
| A61K 39/395 | (2006.01) | |
| C07K 16/28 | (2006.01) | |
| C07K 16/32 | (2006.01) | |
| A61K 45/06 | (2006.01) | |
| A61K 39/00 | (2006.01) | |

(52) U.S. Cl.
CPC ..... *C07K 16/2863* (2013.01); *A61K 39/39558* (2013.01); *A61K 45/06* (2013.01); *C07K 16/32* (2013.01); *A61K 2039/505* (2013.01); *A61K 2039/507* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 5,558,864 A | 9/1996 | Bendig et al. | |
| 5,677,171 A | 10/1997 | Hudziak et al. | |
| 5,821,337 A | 10/1998 | Carter et al. | |
| 6,270,765 B1 | 8/2001 | Deo et al. | |
| 7,226,592 B2 * | 6/2007 | Kreysch ............... | A61K 39/395 424/136.1 |
| 2003/0086924 A1 | 5/2003 | Sliwkowski | |
| 2007/0020261 A1 * | 1/2007 | Sliwkowski ......... | A61K 31/517 424/141.1 |

FOREIGN PATENT DOCUMENTS

| | | |
|---|---|---|
| EP | 0667 165 | 8/1995 |
| EP | 0531 472 | 8/2003 |
| EP | 1362 868 A2 | 11/2003 |
| WO | WO 2004/032960 | 4/2004 |
| WO | WO 2005/077414 | 8/2005 |

OTHER PUBLICATIONS

Haller (Seminars in Oncology, 2002, vol. 29; Suppl 20, p. 31-39).*
Buchler et al (International J of Oncology, 2005, 27:1125-1130).*
Rodeck et al (J of Cellular Biochemistry, 1990, 44:69-79).*
Motoyama et al (Cancer Research, 2002, 62:3151-3158).*
Lu et al (Journal of Biological Chemistry, 2005, 280:19665-19672).*
Arteaga, C.L., "Can Trastuzumab Be Effective Against Tumors With Low HER2/Neu (ErbB2) Receptors?" *J. Clin. Onco.*, 24(33): 3722-3725 (2006).
Bangard, C., et al., "Magnetic Resonance Imaging in an Orthotopic Rat Model: Blockade of Epidermal Growth Factor Receptor with EMD72000 Inhibits Human Pancreatic Carcinoma Growth," *Int. J. Cancer*, 114: 131-138 (2005).
Büchler, P. et al., "Therapy for Pancreatic Cancer with a Recombinant Humanized Anti-HER2 Antibody (Herceptin)," *J. Gastrointest. Surg.*, 5: 139-146 (2001).
Gradishar and Wood, "Advances in Breast Cancer Management," *Kluwer Academic Publishers*, pp. 58-59.
Half, E., et al., "Combination of Cetuximab and Trastuzumab Cooperatively Reduce Cell Growth and Augment NSAID-Mediated Cell Death in Human Colon Cancer Cells," *Gastroenterology*, 130(4)(Suppl. 2): A-184 (2006).
Kim, T ., "Technology Evaluation: Matuzumab, Merck KGaA," *Curr. Opin. Mol. Thera.*, 6(1): 96-103 (2004).
Kuwada, S.K., et al., "Effects of Trastuzumab on Epidermal Growth Factor Receptor-Dependent and—Independent Human Colon Cancer Cells," *Int. J. Cancer*, 109: 291-301 (2004).
Larbouret, C., et al., "In Pancreatic Carcinoma, Dual EGFR/HER2 Targeting with Cetuximab/Trastuzumab is More Effective than Treatment with Trastuzumab/Erlotinib or Lapatinib Alone: Implication of Receptors' Down-Regulation and Dimers' Distribution," *Neoplasia*, 14: 121-130 (2012).
Malkowicz, S.B., et al., "Growth Inhibition of TCC by Combined EGFR and HER2/Neu Antibody Administration," *J. Urology*, 151(5)(Suppl.): 516A (1994).

(Continued)

*Primary Examiner* — Laura B Goddard
(74) *Attorney, Agent, or Firm* — Hamilton, Brook, Smith & Reynolds, P.C.

(57) ABSTRACT

The invention relates to the combined use of anti-EGFR antibodies and anti-Her2 antibodies for the treatment of cancer, especially suitable for cancer expressing high levels of the EGFR type and low levels of HER2. The invention refers in particular monoclonal antibody "trastuzumab" (HERCEPTIN®) directed against the HER2 receptors the efficacy of which can be significantly increased in vivo when combined with monoclonal antibody "matuzumab" (hmAB 425, EMD 72000) directed against EGF receptors. The combination treatment is suitable for patients suffering from cancer having said receptor profile, preferably pancreatic cancer.

15 Claims, 7 Drawing Sheets

(56) References Cited

OTHER PUBLICATIONS

Figure 1:
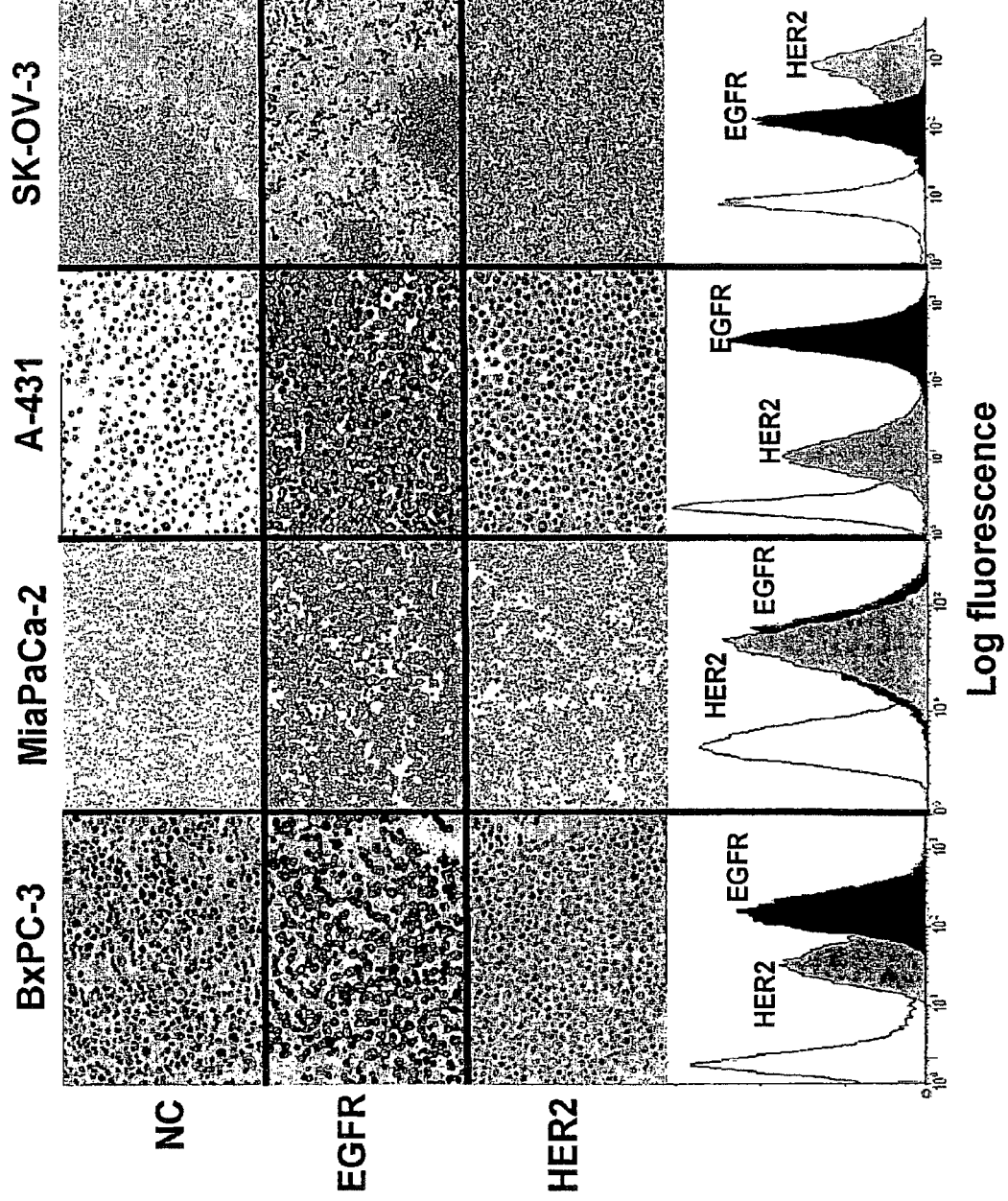

Real, F.X., et al., "Expression of Epidermal Growth Factor Receptor in Human Cultured Cells and Tissues: Relationship to Cell Lineage and Stage of Differentiation," *Can. Res.*, 46: 4726-4731 (1986).

Xiong, H.Q., et al., "Cetuximab, a Monoclonal Antibody Targeting the Epidermal Growth Factor Receptor, in Combination with Gemcitabine for Advanced Pancreatic Cancer: A Multicenter Phase II Trial," *J. Clin. Onco.*, 22(13): 2610-2616 (2004).

Ye, D., et al., "Augmentation of a Humanized Anti-HER2 mAB 4D5 Induced Growth Inhibition by a Human-Mouse Chimeric Anti-EGF Receptor mAB C225," *Oncogene*, 18: 731-738 (1999).

Arnoletti, J.P., et al., "Mechanisms of Resistance to Erbitux (Anti-Epidermal Growth Factor Receptor) Combination Therapy in Pancreatic Adenocarcinoma Cells", Journal of Gastrointestinal Surgery, 8(8): 960-970 (2004).

Azria, D., et al., "Gemcitabine and Ionizing Radiations: Radiosensitization or Radio-Chemotherapy Combination" *Bull Cancer*, 89(4):369-79, (2002).

Azria, D., et al., "Treatment of Untraceable, Locally Advanced Pancreatic Adenocarcinoma with Combined Radiochemotherapy with 5-Fluorouracil and Cisplatin," *Pancreas*, 25(4):360-365, (2002).

Baselga, J., et al., "Phase I Studies of Anti-Epidermal Growth Factor Receptor Chimeric Antibody C225 Alone and in Combination With Cisplatin," *Journal of Clinical Oncology*, 18(4):904-914, (2000).

Baselga, J., et al., "Phase II Study of Weekly Intravenous Recombinant Humanized Anti-p185$^{HER2}$ Monoclonal Antibody in Patients With HER2/*neu*-Overexpressing Metastatic Breast Cancer," *Journal of Clinical Oncology*, 14(3):737-744, (1996).

Bruell, D.A., et al., "Recombinant Anti-EGFR Immunotoxin 425(scFv)-ETA' Demonstrates Anti-Tumor Activity Against Disseminated Human Pancreatic Cancer in Nude Mice," *International Journal of Molecular Medicine*, 15:305-313 (2005).

Büchler, P., et al., "Therapy for Pancreatic Cancer With a Recombinant Humanized Anti-HER2 Antibody (Herceptin)", Journal of Gastrointestinal Surgery, 5(2): 139-146 (2001).

Büchler, P., et al., "Combination Therapy for Advanced Pancreatic Cancer Using Herceptin™ Plus Chemotherapy," *International Journal of Oncology*, 27:1125-1130 (2005).

Czito, B.G., et al., "Increased Toxicity With Gefitinib, Capecitabine, and Radiation Therapy in Pancreatic and Rectal Cancer: Phase I Trial Results," *Journal of Clinical Oncology*, 24(4):656-662, (2006).

Dugan, M.C., et al., "HER-2/neu Expression in Pancreatic Adenocarcinoma: Relation to Tumor Differentiation and Survival," *Pancreas*, 14(3):229-236, (1997).

Friedman, L.M., et al., "Synergistic Down-Regulation of Receptor Tyrosine Kinases by Combinations of mAbs: Implications for Cancer Immunotherapy," *PNAS*, 102(6):1915-1920, (2005).

Goetsch, L., et al., "A Recombinant Humanized Anti-Insulin-Like Growth Factor Receptor Type I Antibody (h7C10) Enhances the Antitumor Activity of Vinorelbine and Anti-Epidermal Growth Factor Receptor Therapy Against Human Cancer Xenografts," *Int. J. Cancer.*, 113:316-328, (2005).

Half, E. et al., "Combination of Cetuximab and Trastuzumab Cooperatively Reduce Cell Growth and Augment NSAID-mediated Cell Death in Human Colon Cancer Cells," Database Biosis [online], Biosciences Information Service, Philadelphia, PA, Biosis No. 200600503002 (Abstract) (Apr. 2006); *Gastroenterology*, 130 (4) *Supp*. 2, p. A184, (Apr. 2006), and Digestive Disease Week Meeting/107$^{th}$ Annual Meeting of the American Gastroenterological Association Institute, Los Angeles, CA (May 20-25, 2006) Abstract #51240.

Haller, D.G., "Future Direction in the Treatment of Pancreatic Cancer," *Seminars in Onclolgy*, 29(6): Supplement 20, pp. 31-39 (2002).

Hynes, N.E. and Lane, H.A., "ERBB Receptors and Cancer: The Complexity of Targeted Inhibitors," *Nature Reviews Cancer*, 5:341-354, (2005).

Klapper, L.N., et al., "The ErbB-2/HER2 Oncoprotein of Human Carcinomas May Function Solely as a Shared Coreceptor for Multiple Stroma-Derived Growth Factors," *Proc. Natl. Acad. Sci. USA*, 96:4995-5000, (1999).

Konecny, G.E., et al., "Activity of the Dual Kinase Inhibitor Lapatinib (GW572016) Against HER-2-Overexpressing and Trastuzumab-Treated Breast Cancer Cells," *Cancer Res.*, 66(3):1630-1639, (2006).

Kumagai, T., et al., "The Role of Distinct p185$^{neu}$ Extracellular Subdomains for Dimerization With the Epidermal Growth Factor (EGF) Receptor and EGF-Mediated Signaling," *PNAS*, 98(10):5526-5531, (2001).

Kuwada, S.K., et al., "Effects of Trastuzumab on Epidermal Growth Factor Receptor-Dependent and—Independent Human Colon Cancer Cells," *Int. J. Cancer*, 109:291-301, (2004).

Leonard, J.P., et al., "Combination Antibody Therapy With Epratuzumab and Rituximab in Relapsed or Refractory Non-Hodgkin's Lymphoma," *Journal of Clinical Oncology*, 23(22):5044-5051, (2005).

Li, J., et al., "Gefitinib ('Iressa', ZD1839), A Selective Epidermal Growth Factor Receptor Tyrosine Kinase Inhibitor, Inhibits Pancreatic Cancer Cell Growth, Invasion, and Colony Formation", International Journal of Oncology, 25: 203-210 (2004).

Li, D., et al., "Pancreatic Cancer," *The Lancet*, 363:1049-1057, (2004).

Mimura, K., et al., "Trastuzumab-Mediated Antibody-Dependent Cellular Cytotoxicity Against Esophageal Squamous Cell Carcinoma," *Clin. Cancer Res.*, 11(13):4898-4904, (2005).

Motoyama, A.B., et al., "The Efficacy of ErbB Receptor-Targeted Anticancer Therapeutics is Influenced by the Availability of Epidermal Growth Factor-Related Peptides," *Cancer Research*, 62:3151-3158 (2002).

Nahta, R., et al., "The HER-2-Targeting Antibodies Trastuzumab and Pertuzumab Synergistically Inhibit the Survival of Breast Cancer Cells," *Cancer Research*, 64:2343-2346, (2004).

Nakamura, H., et al., "Cooperative Cell-Growth Inhibition by Combination Treatment With ZD1839 (Iressa) and Trastuzumab (Herceptin) in Non-Small-Cell Lung Cancer", *Cancer Letters*, 230: 33-46 (2005).

Normanno, N., et al., "Cooperative Inhibitory Effect of ZD1839 (Iressa) in Combination with Trastuzumab (Herceptin) on Human Breast Cancer Cell Growth," *Annals of Oncology*, 13:65-72, (2002).

Overholser, J. P., et al., "Epidermal Growth Factor Receptor Blockade by Antibody IMC-C225 Inhibits Growth of a Human Pancreatic Carcinoma Xenograft in Nude Mice", *Cancer*, 89: 74-82 (2000).

Rodeck, U., et al., "Monoclonal Antibody 425 Inhibits Growth Stimulation of Carcinoma Cells by Exogenous EGF and Tumor-Derived EGF/TGF-α," *Journal of Cellular Biochemistry*, 44:69-79 (1990).

Saxby, A.J., et al., "Assessment of HER-2 Status in Pancreatic Adenocarcinoma," *Am. J. Surg. Pathol.*, 29(9):1125-1134, (2005).

Schlessinger, J., "Ligand-Induced, Receptor-Mediated Dimerization and Activation of EGF Receptor," *Cell*, 110:669-672, (2002).

Schwartz, G., et al., "Phase 2 Clinical Trial Evaluating the Safety and Effectiveness of ABX-EGF in Renal Cell Cancer (RCC)," *Proceedings of ASCO*, 21:24a, Abstract #91 (2002).

Slamon, D. and Pegram, M., "Rational for Trastuzumab (Herceptin) in Adjuvant Breast Cancer Trials," *Seminars in Oncology*, 28(1):13-19, (2001).

Slamon, D.J., et al. "Use of Chemotherapy Plus a Monoclonal Antibody Against HER2 for Metastatic Breast Cancer That Overexpresses HER2," *The New England Journal of Medicine*, 344(11):783-792, (2001).

Tobita, K., et al., "Epidermal Growth Factor Receptor Expression in Human Pancreatic Cancer: Significance for Liver Metastasis," *International Journal of Molecular Medicine*, 11:305-309, (2003).

Tonra, J.R., et al., "Synergistic Antitumor Effects of Combined Epidermal Growth Factor Receptor and Vascular Endothelial Growth Factor Receptor-2 Targeted Therapy," *Clin. Cancer Res.*, 12(7):2197-2207, (2006).

Tzahar, E. and Yarden, Y., "The ErbB-2/HER2 Oncogenic Receptor of Adenocarcinomas: From Orphanhood to Multiple Stromal Ligands," *Biochimca et Biophysica Acta*, 1377:M25-M37, (1998).

(56) References Cited

OTHER PUBLICATIONS

Wagner, M., et al., "Curative Resection is the Single Most Important Factor Determining Outcome in Patients with Pancreatic Adenocarcinoma," *British Journal of Surgery*, 91:586-594, (2004).
Yarden, Y. and Sliwkowski, M.X., "Untangling the ErbB Signalling Network," *Nature Reviews, Molecular Cell Biology*, 2:127-137, (2001).
Ye, D., et al., "Augmentation of a Humanized Anti-HER2 mAb 4D5 Induced Growth Inhibition by a Human-Mouse Chimeric Anti-EGF Receptor mAb C225," *Oncogene*, 18:731-738, (1999).
International Search Report for PCT/EP2006/012133, "Combination Therapy Using Anti-EGFR and Anti-HER2 Antibodies," dated Apr. 12, 2007.
Written Opinion for PCT/EP2006/012133, "Combination Therapy Using Anti-EGFR and Anti-HER2 Antibodies," dated Apr. 12, 2007.
International Preliminary Report on Patentability for PCT/EP2006/012133, "Combination Therapy Using Anti-EGFR and Anti-HER2 Antibodies," dated Jul. 8, 2008.

\* cited by examiner

Days post graft

COMBINATION THERAPY USING ANTI-EGFR AND ANTI-HER2 ANTIBODIES

RELATED APPLICATIONS

This application is a continuation of U.S. application Ser. No. 12/086,725, which is the U.S. National Stage of International Application No. PCT/EP2006/012133, filed on Dec. 15, 2006, published in English, which claims priority under 35 U.S.C. §119 or 365 to European, Application No. 06000107.0, filed Jan. 4, 2006. The entire teachings of the above applications are incorporated herein by reference.

FIELD OF THE INVENTION

The invention relates to the combined use of an anti-EGFR (ErbB1) antibody and an anti-Her2 (ErbB2) antibody for the treatment of cancer. The invention furthermore relates to the treatment of tumor in an individual with said antibodies, wherein the tumor cells express high levels of the EGFR type and low or no significant levels of HER2. In particular, the invention refers to the combination treatment using monoclonal antibody trastuzumab" (HERCEPTIN®) directed against HER2 receptor and "matuzumab" (hmAb 425, EMD 72000) directed against EGF receptor, or another anti-EGFR antibody. The combination treatment is preferably suitable for patients suffering from a cancer, the tissue of which do not overexpress HER2 or express HER2 in low amounts, but do overexpress EGFR.

BACKGROUND OF THE INVENTION

Subclass I of the receptor tyrosine kinase (RTK) super family consists of ErbB receptors and comprises four members: EGFR/ErbB1, HER2/ErbB2, ErbB3 and ErbB4. All members have an extracellular ligand-binding region, a single membrane-spanning region and a cytoplasmic tyrosine-kinase-containing domain. Tyrosine kinases are a class of enzymes that catalyze the transfer of the terminal phosphate of adenosine triphosphate to tyrosine residues in protein substrates.

The ErbB receptors are expressed in various tissues of epithelial, mesenchymal and neuronal origin. Under normal conditions, activation of the ErbB receptors is controlled by the spatial and temporal expression of their ligands, which are members of the EGF family of growth factors. Ligand binding to ErbB receptors induces the formation of receptor homo- and heterodimers and activation of the intrinsic kinase domain, resulting in phosphorylation on specific tyrosine kinase residues within the cytoplasmic tail. These phosphorylated residues serve as docking sites for various proteins, the recruitment of which leads to the activation of intracellular signaling pathways.

EGFR and HER2 are known to play an essential role in regulating cell proliferation and differentiation. They have a strong tendency to assemble with other HER receptors into homo- and/or heterodimers upon extracellular growth factor binding, which results in various forms of signal transduction pathways activation, leading to either apoptosis, survival, or cell proliferation. Mounting evidence suggests that not only receptor expression or receptor overexpression but also communication among HER receptors plays a crucial role in tumor behavior (Kumagai et al., 2001, PNAS 98, 5526). In particular, binding of receptor-specific ligands to the ectodomain of EGFR often results in the recruitment of HER2, as the preferred heterodimerization partner (e.g. Klapper et al., 1999, PNAS 96, 4995). As HER2 is the only HER family member that does not bind a known specific ligand, its principal biological function, as a signal transducer, appears to result from its participation in heterodimeric receptor complexes with EGFR or other HER receptors (e.g. Konecny et al., 2006, Cancer Res. 96, 1630).

Recent studies (J. Schlessinger, 2002, Cell 110, 669) show that receptor dimerization is mediated by receptor-receptor interactions in which a loop protruding from neighboring receptors mediates receptor dimerization and activation. Receptor dimerization is essential for stimulating of the intrinsic catalytic activity and for the self-phosphorylation of growth factor receptors on tyrosine residues.

It should be remarked that receptor protein tyrosine kinases are able to undergo both homo- and heterodimerization, wherein homodimeric receptor combinations are less mitogenic and transforming (no or weak initiation of signaling) than the corresponding heterodimeric combinations. Heterodimers containing ErbB2 are the most potent complexes (Yarden and Sliwkowski, 2001, Nature Reviews, Molecular cell Biology, volume 2, 127-137; Tzahar and Yarden, 1998, BBA 1377, M25-M37).

Two important types of ErbB inhibitor are in clinical use: chimeric, humanized or fully human antibodies directed against the extracellular domain of EGFR or ErbB2, and small-molecule tyrosine-kinase inhibitors (TKIs) that compete with the ATP in the tyrosine-kinase domain of the receptor.

The use of mAbs binding with high affinity to these two members of the ErbB (HER) family, EGFR and HER2, thus appears to be rational for the development of new cancer therapy strategies which would have the potential to inhibit the receptor dimerization. Until now, however, each of the two mAbs have been used in cancer therapy individually in conjunction with various chemotherapeutic drugs (Slamon et al., 2001, New Engl. J. Med 344, 783; Baselga et al., 2000, J Clin Oncol. 18, 904) or more recently in association with different drugs having tyrosine kinase receptor inhibition properties (e.g. Normanno et al., 2002, Ann Oncol 13, 65) The action of small tyrosine kinase inhibitor molecules, however, cannot be compared with the potential biological activity induced by the binding of a high molecular weight antibody molecule.

The mechanism of anti-tumor activity of individual anti-ErbB/HER receptor mAbs is not entirely understood. A series of experimental results in mice KO for the Fc receptor strongly suggested that most of the anti-tumor effect was due to the recruitment of effector NK cells by an antibody dependent cell-mediated cytotoxic (ADCC) mechanism. However, the evidence of inhibition of receptor phosphorylation and receptor internalization induced on tumor cells by the anti-ErbB/HER receptor mAbs argues in favor of an apoptotic or cytostatic signal transduced through the receptor (e.g. Friedman et al., 2005, PNAS 102, 1915).

There are several anti-HER/ErbB antibodies in clinical studies and already approved and on market, for example matuzumab, cetuximab, panitumumab and trastuzumab.

Humanized monoclonal antibody 425, also designated as matuzumab (hMAb 425, U.S. Pat. No. 5,558,864; EP 0531 472) and chimeric monoclonal antibody 225 (cMAb 225), both directed to the EGF receptor, have shown their efficacy in clinical trials.

The c225 antibody (cetuximab, ERBITUX®) was demonstrated to inhibit EGF-mediated tumor cell growth in vitro and to inhibit human colorectal tumors in vivo received marked approval in 2003. The antibody as well as in general all anti-EGFR antibodies, appear to act, above all, in synergy with certain chemotherapeutic agents (i.e., doxorubicin, adriamycin, taxol, and cisplatin) to eradicate human tumors in vivo in xenograft mouse models (e.g. EP 0667165). Furthermore, it could be shown that the combination of the anti-EGFR antibody c225 with the second anti-EGFR antibody matuzumab shows a synergistic effect in vitro models, indicating that these two antibodies directed to the same receptor bind to different epitopes of EGFR (WO 2004/032960).

The mouse antibody 4D5 directed to the HER2/ErbB2 was further found to sensitize ErbB2-expressing breast tumor cell lines to the cytotoxic effects of TNFα (U.S. Pat. No. 5,677,171). A recombinant humanized version, designated as huMAb4D5-8, rhuMAb HER2, trastuzumab, or HERCEPTIN® (U.S. Pat. No. 5,821,337) is clinically active in patients with ErbB2-overexpressing metastatic breast cancers that have received extensive prior anti-cancer therapy (Baselga et al., *J. Clin. Oncol.* 14:737-744 (1996)). HERCEPTIN® received marketing approval in 1998 for the treatment of patients with metastatic breast cancer whose tumors overexpress the ErbB2 protein.

Although, as stated above, the therapeutic efficacy trastuzumab in breast carcinoma is well demonstrated, it is strictly limited and only approved for 30% of breast cancer patients whose tumor overexpress HER2. 70% of the breast cancer patients do not or insufficiently respond to trastuzumab because their individual tumor do not overexpress or do not sufficiently express HER2. In other cancers and or individual cancers, HER2 is overexpressed in a significant percentage of cases ranging from 43-69%, whereas EGFR is usually overexpressed in a range from 45-95%. However, as a rule, the levels of HER2 expression are in principal low in the majority of tumors. Furthermore, the overexpression of EGFR and HER2 receptors is often caused by encoding gene amplification (Hynes et al., 2005, Nat Rev Cancer 5, 341). Thus, the present day consensus is that anti-HER2 mAb is inefficient in tumors with low HER2 expression or missing overexpression, which is the case, for example, for most pancreatic carcinoma in the clinic (e.g. Saxby et al., 2005, J Surg Pathol 29, 1125).

Panitumumab (VECTIBIX®) is a fully human anti-EGFR antibody and has recently received marked approval in the US (Schwartz et al., 2002, Proc. Am Soc Clin Oncol 21, 24).

Adenocarcinomas of the pancreas remain one of the most difficult malignancies to treat. The incidence has steadily increased over the past four decades, and its prognosis is still dismal, despite tremendous efforts in early diagnosis and therapy. At the time of diagnosis, the majority of patients (80-90%) have locally or metastatic tumors. Even with a complete surgical resection, the five-year survival rate is less than 20% (Wagner et al., Br J Surg 2004; 91: 586-94). The conventional therapy associating both surgery and radiotherapy alone or in combination with chemotherapy shows modest efficacy in local control and palliation, and no real progress in patient survival (Azria et al., Bull Cancer 2002; 89: 369-79, Azria et al., Pancreas 2002; 25: 360-5, Li et al. Lancet 2004; 363:1049-57.2-4). Accordingly, novel approaches to human pancreatic carcinoma therapy are urgently needed.

It is well documented that pancreatic adenocarcinomas and displasias frequently overexpress tyrosine kinase receptors. Overexpression of EGFR in pancreatic cancer is associated with advanced disease at presentation and reduced median survival time. The significance of HER2 expression/overexpression in pancreatic cancer prognosis is not as clear. Indeed, no correlation between tumor differentiation degree and the level of HER2 expression in human pancreatic specimens has been reported (Dugan et al., Pancreas 1997; 14: 229-36). This might be explained by recalling that the level of HER2 does not mediate mitogenesis by itself and that heterodimerisation has to be activated.

The concept of blocking EGFR and HER2 is in principal known and has been applied in other models expressing high levels of EGFR and/or HER2. An additive but not an synergistic effect on reducing cell proliferation in vitro was shown using combined treatment either with chimeric anti-EGFR antibody mAb c225 (cetuximab) and humanized anti-HER2 antibody 4D5 (trastuzumab) on the human ovarian cancer cell line OVCAR 420 (Ye et al. 1999, Oncogene 18, 731) or with trastuzumab and the murine variant of mAb 225 on EGFR-dependent colon cancer cell lines (Kuwada et al., Int J Cancer 2004; 109: 291-301).

Furthermore, different groups addressed the simultaneous attack of HER1 and HER2 by associating the chemical EGFR kinase inhibitor ZD1839 (Iressa) with trastuzumab (Normanno et al., Ann Oncol 2002; 13: 65-72) and found that in the cell lines SK-BR-3 and BT-474 the combination of these latter compounds induces a better anti-proliferative effect than the two compounds used separately, particularly in terms of induction of apoptosis.

However, little information is available concerning antibody efficacy and the actual function of EGFR and HER2 receptors in specific cancer tissue expressing low levels of at least one of these receptors, for example, pancreatic cancer, targeted by specific anti-ErbB antibodies, and up to date no clinical studies have evaluated the efficacy of targeting concurrently these two receptors in these tumors with suitable monoclonal antibodies.

Based on the lack of an effective therapy and implication of EGFR and HER2 in specific cancer expressing low levels of at least one of these two types of receptor, there is a motivation of blocking EGFR and HER2 simultaneously in a cancer specific model in which preferably a high EGFR expression and no significant or low-level expression is presented, wherein said expression pattern is evaluated by immunocytochemical analysis or by using flow cytometry analysis technique.

SUMMARY OF THE INVENTION

According to the current invention it could be shown that the combination of an anti-HER2 antibody, such as trastuzumab, with an anti-EGFR antibody, such as matuzumab, provides in vivo tumor regression or at least reduced and/or delayed tumor growth in vivo, however preferably only in cancers and tumor tissues that expresses no significant or low levels of HER2, and preferably high levels of EGFR. Such a different expression pattern between said ErbB receptors can be found in many cancers, such as pancreatic cancer. The different expression pattern of a specific tumor tissue may be also an individual property. In other words, it is possible, that a specific tumor develops a different expression pattern regarding said HER/ErbB receptors in different individuals/patients suffering from said tumor.

Surprisingly, the combined treatment of an anti-Her2 antibody such as trastuzumab, with a suitable anti-EGFR antibody, such as matuzumab, for cancer therapy is strongly synergistic, if the treated cancer overexpresses EGFR but not HER2, or, if the treated cancer does not or not significantly express HER2 (low level expression) and does express EGFR with levels higher than in corresponding normal (non-tumor) tissue.

The efficacy of such a combination treatment is synergistically increased if, in addition, the anti-HER2 antibody used has no or no significant capability to inhibit HER2 dimerization, but the anti-EGFR antibody used does have the capability to inhibit significantly EGFR dimerization.

These finding are novel and not foreseeable even in view of the prncipally known concept of blocking EGFR and HER2, or EGFR and EGFR by different epitopes as described above.

The synergistic effect of the combination is very distinct when the individual cancer does not overexpress HER2 but does overexpress EGFR.

The synergistic effect described according to the invention on tumor growth with, for example, trastuzumab (Herceptin) and matuzumab (EMD72000) may be explained, without being bound to any theory or hypothesis, by different mechanistic actions of each antibody on EGFR/HER2 heterodimerization: According to the invention trastuzumab, and any potential functionally similar anti-HER2 antibody, is thought according to the invention to bind to domain IV in a way that does not inhibit dimerization, but instead appears to enhance the endocytosis of HER2 receptor and its disappearance from the cell membrane. In contrast to that, EMD72000, and any potential functionally similar anti-EGFR antibody, is thought to directly inhibit dimerization of EGFR. Natha et al. (Cancer Res 2004; 64: 2343-6) found that trastuzumab and another anti-Her2 antibody called pertuzumab act synergistically. Since pertuzumab is known to inhibit HER2 dimerization, anti-EGFR antibody matuzumab, and any other functionally similar anti-EGFR antibody, could surprisingly play according to this invention an analogous role in EGFR dimerization.

The findings of this invention show and confirm the importance of communication between the different HER/ErbB receptors. HER2 has been shown to act as a favorite co-receptor in partnership with the other members of the HER family, with an improvement of the signaling potency of its dimerization partner on multiple levels.

According to the results of the present invention, the strategy of simultaneously targeting EGFR and HER2 by suitable monoclonal antibodies may lead under specific prerequisites to a therapeutic benefit providing synergistic efficacy in biological systems with low HER2 receptor expression under pathological conditions. According to this invention, the impact and efficacy of suitable combined EGFR/HER2 monoclonal antibodies seems to be dependent not only on their respective receptor expression but also on their capability of their the homo- and/or heterodimerization potential of the cells. These results are novel and not foreseeable even if considered in context with the known concept of blocking EGFR and HER2 or EGFR and EGFR by different epitopes (see above).

In view of the present demonstration of the synergistic therapeutic effect of two anti-EGFR and -HER2 mAbs on two pancreatic carcinoma lines with moderate expression of HER2 and one ovarian carcinoma line overexpressing both HER receptors, the extent to which these experimental results may have an impact on the management of pancreatic and other types of carcinomas are considered. In pancreatic carcinoma, both EGFR and HER2 are known to be expressed in a significant percentage of the cases (e.g. Tobita et al., 2003, Int J Mol Med 11, 305) and expression of these receptors has been shown to be involved in the initiation and progression of this tumor.

Thus, in view of the toxicity and very modest results of the most advanced and intensive regimens of chemo- and radiotherapy in this type of cancer (e.g. Czito et al., 2006, J Clin Oncol 24, 656) it would desirable to consider a combined treatment with the two anti-EGFR and anti-HER2 mAbs in patients with carcinomas expressing even low levels of at least one of the two HER receptors. For the anti-HER2 mAb, it has been well established that the clinical benefits are limited to tumors with marked overexpression of the receptor (Slamon et al., 2001, Semin Oncol 28, 13), whereas by the present experiments, the synergism of specific anti-HER2 antibody with specific anti-EGFR antibody was demonstrated on two pancreatic carcinomas with low to moderate HER2 expression.

It has been shown in various carcinoma cell lines that treatment with small molecules inhibiting tyrosine kinase receptors, such as Iressa for EGFR (Normanno et al., 2002, ann Oncol 13, 65) or the dual kinase inhibitor lapatinib for both EGFR and HER2 (Konecny et al., 2006, Cancer Res 66, 1630), can have a synergistic effect with anti-HER2 mAb treatment. However, the synergistic effect was mainly demonstrated in vitro and exclusively on target carcinoma lines overexpressing HER2. Furthermore, the effect of a small molecule with typrosine kinase inhibitory property cannot be considered as identical to that of a large antibody molecule binding to the external domain of the receptors.

For many years, several groups presented in vitro studies on tumor cells suspensions showing that simultaneous incubation with the two anti-EGFR and -HER2 mAbs induced more efficient inhibition of receptor phosphorylation and/or specific internalisation of the receptors, than incubation with one mAb alone (21-24). However, only one of the groups (23) tried a limited in vivo study but failed to demonstrate any synergism between the two mAbs.

Thus, the results presented herein represent the first time in vivo experimental demonstration of a long expected new improvement of cancer therapy by the synergistic action of two anti-EGFR and HER2 mAbs. Furthermore, the results presented here suggest that a patient having breast carcinoma with moderate expression of HER2, who could not be treated with anti-HER2 mAb therapy, might benefit from the synergic treatment of the two anti-HER/ErbB mAbs, provided that the tumor also expresses EGFR.

Three other cancer treatments based on the synergistic effect of two mAbs of different specificities are presently under investigation. First, a phase I clinical trial is underway for the treatment of non-Hodgkin's lymphoma with a combination of anti-CD20 and CD22 mAbs (Leonard et al., 2005, J Clin Oncol 23, 5044). The antigens recognized by these two mAbs are very different, however, and do not have the heterodimerization property, that is characteristic for the two HER receptors antibodies targeted in our study.

A second, entirely experimental, study involves an anti-insulin-like growth factor receptor (IGF-IR) mAb, which is reported to have a synergistic anti-tumor effect, either with a chemotherapeutic agent (vinorelbine) or with an anti-EGFR mAb, in a breast and a lung carcinoma xenograft model (Goetsch et al., 2005, Int J Cancer 113, 316). However, the IGF-IR does not belong to the HER receptor family and in terms of potential treatment, application IGF-IR is less tumor restricted than is the HER2 receptor.

A third experimental study involves an anti-EGFR and an anti-VEGFR mAb in a pancreatic carcinoma xenograft model (Tonra et al., 2006, Clin Cancer Res 12, 2197)). The two mAbs used in this study are not directed against the same tumor target cells. Indeed, anti-VEGFR mAb binds to a receptor, which is expressed on endothelial cells, but not on pancreatic carcinoma cells. Thus the mechanism of action of the two mAbs in that study appears to be related to tumor vascularization parameters and is distinct from the binding of the two mAbs on two HER/ErbB receptors located on the same target carcinoma cells, which seems responsible for the synergistic anti-tumor effect presented here.

In summary the invention relates to the following:
In summary the invention relates to A pharmaceutical composition comprising an anti-EGFR antibody and an anti-HER2(ErbB2) antibody or an immunologically effective fragment thereof in an effective amount optionally together with a pharmaceutically carrier, diluent or excipient, wherein the anti-EGFR antibody is murine, chimeric or humanized mAb 425 (matuzumab, EMD72000) and the anti-HER2 antibody is murine, chimeric or humanized mAb 4D5 (trastuzumab, HERCEPTIN®), preferably the humanized variants of each of said antibodies.

A corresponding pharmaceutical composition wherein said anti-EGFR antibody binds to tumor cells, wherein the EGF receptor is moderately or highly expressed or overexpressed.

A corresponding pharmaceutical definition wherein said anti-HER2 antibody binds to tumor cells, wherein the HER2 receptor expression is low, or lower than EGFR expression A corresponding pharmaceutical composition, wherein the tumor cells are pancreatic tumor cells.

A corresponding pharmaceutical composition comprising additionally a cytotoxic agent.

A corresponding pharmaceutical composition wherein the cytotoxic agent is a chemotherapeutic agent, preferably selected from the group consisting of cisplatin, doxorubicin, gemcitabine, docetaxel, paclitaxel, bleomycin and irinotecan.

A corresponding pharmaceutical composition, wherein the cytotoxic agent is a third ErbB receptor inhibitor, a VEGF receptor inhibitor, a tyrosine kinase inhibitor, a protein kinase A inhibitor, an anti-angiogenic agent, or a cytokine.

A corresponding pharmaceutical composition, wherein one or each of said antibodies are fused at its C-terminus to a biologically effective peptide, polypeptide or protein, optionally via a linker peptide, to form a immunocnjugate, preferably an immunocytokine.

A pharmaceutical kit comprising (i) a first package comprising an anti-EGFR antibody or an anti-EGFR antibody immunoconjugate as specified above or an immunologically effective portion thereof, and (ii) a second package comprising an anti-HER2 antibody or an anti-HER2 antibody immunoconjugate as specified above or an immunologically effective portion thereof.

A corresponding pharmaceutical kit comprising (iii) a third package comprising a cytotoxic agent as specified above.

The use of a pharmaceutical composition as specified above for the manufacture of a medicament for the treatment of tumors expressing ErbB receptors.

The corresponding use of said pharmaceutical composition, wherein said tumor does not overexpress HER2 or does express Her2 only in lower amounts than EGFR.

The corresponding use of said pharmaceutical composition, wherein said tumor cells overexpress EGFR but not HER2.

The corresponding use of said pharmaceutical composition for the treatment of pancreatic cancer.

The uses of all pharmaceutical compositions as described for the manufacture of a medicament directed against cancer in combination with radiotherapy and/or chemotherapy.

A pharmaceutical composition comprising any anti-EGFR antibody and any anti-HER2 antibody in a general aspect and principle of the invention, wherein said antibodies alone do not inhibit heterodimerization of EGFR and HER2, but do so if given in combination.

A corresponding pharmaceutical composition, wherein the anti-EGFR antibody binds to tumor cells to be treated that overexpress EGFR, and the anti-Her2 antibody binds to tumor cells to be treated that do not overexpress HER2, or do express HER2 in a low or moderate amount compared to said EGFR overexpression.

A corresponding pharmaceutical composition, wherein said anti-EGFR antibody is selected from the group of murine, chimeric or humanized mAb 425 (matuzumab) and said anti-HER2 antibody is selected from the group od murine chimeric or humanized mAb 4D5 (trastuzumab).

A bispecific antibody comprising a first antigen binding site that binds to EGFR, preferably deriving from murine, chimeric or humanized mAb 425 (matuzumab), and a second antigen binding site that binds to HER2, preferably deriving from murinde, chimeric or humanized mAb 4D5 (trastuzumab).

A use of a pharmaceutical composition comprising an anti-HER2 antibody and an anti-EGFR antibody for the manufacture of a medicament for the treatment of cancer in an individual, wherein said cancer in said individual expresses EGFR and HER2, wherein HER" is expressed in low levels or levels that are not sufficient to respond significantly to anti-HER2 antibody treatment alone.

A corresponding use, wherein said anti-HER2 antibody, when given alone, does not or not significantly inhibit HER2 dimerization and/or HER2/EGFR heterodimerization, and said anti-EGFR antibody, when given alone, does significantly inhibit EGFR dimerization and/or EGFR/HER2 heterodimerization.

A corresponding use, wherein said cancer does not overexpress HER2 and/or does not overexpress EGFR.

A corresponding use, wherein said anti-HER2 antibody is murine, chimeric or humanized mAb 4D5 (trastuzumab).

A corresponding use, wherein said anti-EGFR antibody is murine, chimeric or humanized mAb 425 (matuzumab).

A corresponding use, wherein said anti-HER2 antibody is murine, chimeric or humanized mAb 4D5 (trastuzumab) and said anti-EGFR antibody is murine, chimeric or humanized mAb 425 (matuzumab).

A corresponding use, wherein said cancer is pancreatic cancer or breast cancer.

A corresponding use, wherein said antibodies are immunologically effective fragments, such as Fab'-(Fab')2 fragments.

A corresponding use, wherein additionally a cytotoxic agent is administered, for example a chemotherapeutic agent, preferably selected from the group consisting of cisplatin, doxorubicin, gemcitabine, docetaxel, paclitaxel, bleomycin and irinotecan, or a VEGF receptor inhibitor, a small molecule tyrosine kinase inhibitor, an anti-angiogenic agent, or a cytokine.

A corresponding use, wherein one or both of said antibodies are fused preferably at its C-terminus to a biologically effective peptide, polypeptide or protein, optionally via a linker peptide, thus forming an immunocnjugate.

A corresponding use, wherein said immunoconjugate is an immunocytokine.

A corresponding use, comprising a bispecific antibody having the specificities of the two antibodies as specified above and below.

A use of a pharmaceutical composition comprising an anti-HER2 and an anti-EGFR antibody for the manufacture of a medicament for improving the efficacy of the treatment of cancer in an individual with said anti-HER2 antibody, wherein said cancer in said individual expresses HER2 in low levels or leves that are not sufficient to respond significantly to said anti-HER2 antibody treatment alone, and EGFR in levels that are sufficient to respond significantly to an anti-EGFR-antibody, A corresponding use, wherein said anti-HER2 antibody, when given alone, does not or not significantly inhibit HER2 dimerization and/or HER2/EGFR heterodimerization, and said anti-EGFR antibody, when given alone, significantly inhibits EGFR dimerization and/or EGFR/HER2 heterodimerization.

A corresponding use, wherein in said cancer HER2 is not overexpresses and EGFR is overexpressed.

A corresponding use, wherein said anti-HER2 antibody is murine, chimeric or humanized mAb 4D5 (trastuzumab) and said anti-EGFR antibody is murine, chimeric or humanized mAb 425 (matuzumab).

A corresponding use, wherein said cancer is pancreatic or breast cancer.

A method for treating cancer that expresses HER2 and EGFR in an individual, wherein said cancer in said individual expresses HER2 in levels that are not sufficient to respond significantly to an anti-HER2 antibody, when given alone to the individual, the method comprising administering to the individual an anti-HER2 antibody, which, when given alone, does not or not significantly inhibit HER2 dimerization and/or HER2/EGFR heterodimerization, and an anti-EGFR antibody, which, when given alone, significantly inhibits EGFR dimerization and/or EGFR/HER2 heterodimerization.

A corresponding method, wherein HER2 is not overexpressed and/or EGFR is overexpressed.

A corresponding method, wherein said anti-HER2 antibody is murine, chimeric or humanized mAb 4D5 (trastuzumab)

A corresponding method, wherein said anti-EGFR antibody is murine, chimeric or humanized mAb 425 (matuzumab).

A corresponding method, wherein said anti-HER2 antibody is murine, chimeric or humanized mAb 4D5 (trastuzumab) and said anti-EGFR antibody is murine, chimeric or humanized mAb 425 (matuzumab).

A corresponding method, said cancer is pancreatic or breast cancer.

A method for improving the efficacy of the treatment of cancer that expresses HER2 and preferably overexpresses EGFR with an anti-HER2 antibody, wherein said cancer does not overexpress HER2 or expresses HER2 in low levels or levels that are not sufficient to respond significantly to said anti-HER2 antibody treatment alone; the method comprising administering to an individual an anti-HER2 antibody, which, when given alone, does not or not significantly inhibit HER2 dimerization and/or HER2/EGFR heterodimerization, and an anti-EGFR antibody, which, when given alone, significantly inhibits EGFR dimerization and/or EGFR/HER2 heterodimerization.

A corresponding method, wherein said anti-HER2 antibody is murine, chimeric or humanized mAb 4D5 (trastuzumab), and/or said anti-EGFR antibody is murine, chimeric or humanized mAb 425 (matuzumab).

A corresponding method, wherein the cancer is pancreatic cancer or breast cancer.

DETAILED DESCRIPTION

EGFR and HER2 Receptor Cell Surface Expressions: Immunocytochemical analyses on human pancreatic carcinoma BxPC-3 cells show a high level of EGFR (classified as +++) but no detectable levels of HER2 receptor expression, as compared with human carcinoma ovarian cells SK-OV-3 and epidermal carcinoma reference cells A-431, classified as +++ for HER2 and +++ for EGFR, respectively, by the same analysis (FIG. 1).

A second pancreatic cancer cell line MiaPaCa-2 is also classified negative for HER2 and ++ for EGFR.

In contrast, using the more sensitive flow cytometry technique (Mimura et al., 2005, Clin Cancer Res 11, 4898), a moderate expression of HER2 can be found on BxPC-3 and MiaPaCa-2 cells as compared with SK-OV-3 cells.

The overexpression of EGFR by BxPC-3 cells can be confirmed but at a slightly lower level than the reference A-431 cells. MiaPaCa-2 show a moderate and equal expression of both EGFR and HER2 receptors. SK-OV-3 show a moderate expression of EGFR and a high expression of HER2 (FIG. 1).

Based on the quite low expression level of HER2 on the BxPC-3 tumor cells and on the biodistribution results the limited tumor activity of trastuzumab obtained in vitro and in vivo could be expected. Indeed, overexpression of HER2 is an established diagnostic tool to evaluate breast cancer patients for trastuzumab therapy (Slamon et al., 2001, Semin Oncol; 28, 13), and accordingly, only patients with immunohistochemical 3+HER2-tumor expression benefit from this targeting therapy.

Infrequent HER2/neu overexpression may explain why trastuzumab is not currently used in the clinic for the treatment of pancreatic cancer. Studies confirmed the incapacity of monotherapy of trastuzumab to slow tumor growth presenting low HER2 expression. It should be noted that the doses of trastuzumab used in these studies are three-to-twelve fold higher than those used in the experiments according to the invention.

Anti-Tumor Activity of Matuzumab and/or Trastuzumab Against Two Pancreatic and an Ovarian Carcinoma Xenografts.

The therapeutic efficacy of the anti-EGFR and anti-HER2 mAbs alone or in combination is first tested on BxPC-3 xenografts in nude mice. To evaluate the different forms of mAb therapy on tumor xenografts of various sizes, two series of representative experimental results, first on tumors of relatively small volume (77±49 mm3, experiment S) and second with larger tumors (503±205 mm3, experiment L), are analyzed. Results from experiment S (FIG. 2), obtained in groups of eight mice treated with 50 µg of each antibody twice weekly for four weeks, show a significantly higher inhibition of tumor growth in the combined antibody group as compared to the groups treated with each antibody alone (P=0.002). Further analysis of the same experimental results show that the tumor increment factors at the end of treatment are markedly higher in the mice treated with anti-EGFR and anti-HER2 mAb alone, 4.9±2.1 and 6.4±4.4, as compared with the combined mAb group 0.7±0.5 (Table 1, upper part).

Furthermore, only the combined mAb treatment induces two complete tumor remissions. Results from an additional experiment on mice with similar size BxPC-3 xenografts treated with fourfold greater doses of each mAb (200 µg) alone or in combination entirely confirm the previous results, with tumor increment factors much higher for the single mAb treatment, as compared with the combined mAb therapy (Table 1, lower part).

TABLE 1

Increment factor of BxPC-3 xenograft volume at the end of treatment

| mAb | Treatment[a] | Increment fact[b] | % tumor free mice |
|---|---|---|---|
|  — | C | 8.0 ± 4.0 | 0 |
| 50 | M | 4.9 ± 2.1 | 0 |
|  | T | 6.4 ± 4.4 | 0 |
|  | T + M | 0.7 ± 0.5 | 25 (2/8) |
|  — | C | 21.3 ± 7.0 | 0 |
| 200 | M | 4.3 ± 2.8 | 0 |
|  | T | 5.5 ± 2.1 | 0 |
|  | T + M | 0.8 ± 0.3 | 60 (3/5) |

[a]C: control, M: matuzumab, T: trastuzumab, T + M: both mAbs.
[b]Increment factor: (tumor volume at the end of treatment)/(tumor volume at the beginning of treatment).

Figure 3A:
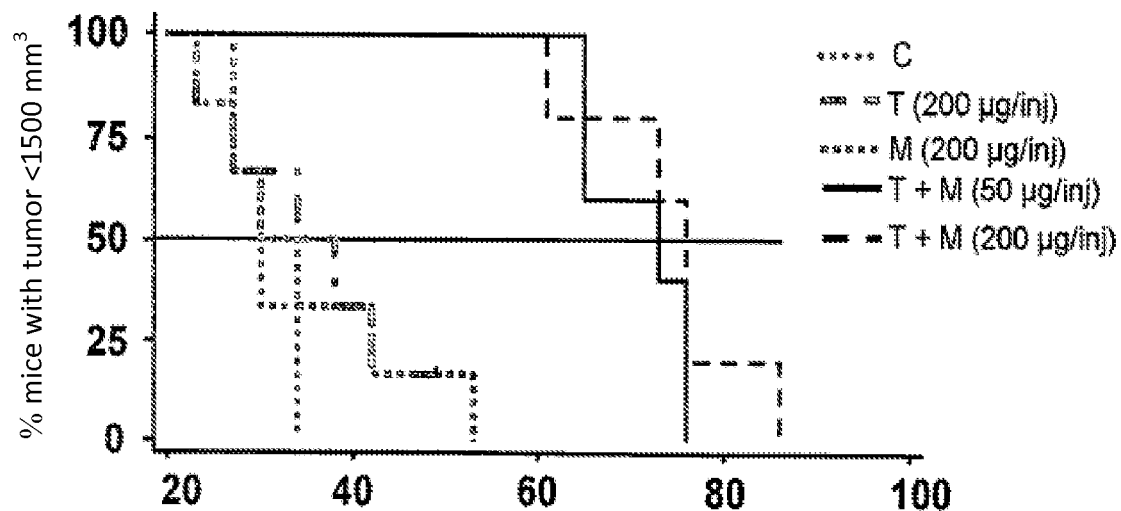

In addition, complete tumor remissions in three out of five mice are observed only in the combined therapy group at the end of treatment. Comparison of therapy with different antibody doses, reported in Table 1, show that 50 µg of each mAb in combination induced markedly lower tumor increments (0.7+/−0.5) than those obtained in mice treated with fourfold greater doses of the single mAb (4.3 and 5.5). No detectable dose effect can be observed between the 50 and 200 µg treatments suggesting that the synergism of the two mAbs binding to the two HER receptors are more important than the absolute amounts of antibody. This observation is clearly in favor of a synergic effect rather than an additive one. Results from larger xenografts from the BxPC-3 tumors (experiment L) obtained in four groups of six mice injected with 200 µg of each antibody show in adapted Kaplan-Meier survival curves (FIG. 3A) that the median delay for tumors to reach 1500 mm$^3$ volume is significantly longer (73 days) in mice treated with the mAb combination than in mice treated with only one mAb (anti-HER2, 30 days, anti-EGFR, 34 days) P=0.001. The time tumor progression curves from the same experiment (FIG. 3B) confirm that the time to reach a threefold larger tumor is significantly longer (P<0.001) for the combined treatment group, than for the two single mAb treatments. Interestingly, in an additional group of six mice with large tumors treated with only 50 µg of each mAb in combination, the time (70 days) for the tumor to reach a volume of 1500 mm3 is much longer as compared with the tumors in the group treated with 200 µg of each mAb alone (30 and 34 days) (FIG. 3A). This confirms that even with the larger tumors the double specificity of the two mAb is more effective than the absolute mAb doses and that the greater anti-tumor effect is due to a synergistic rather than an additive effect of the two mAbs. The tumor growth inhibition property of the combined anti-EGFR and anti-HER2 mAbs is further tested on xenografts from a second human pancreatic carcinoma line MiaPaCa-2, which also expresses low HER2 levels. Injection twice a week of 50 µg of each mAb alone or in combination is initiated in groups of six mice when the mean tumor volume has reached 64 mm3±5 and continued for four weeks. Animals were euthanized when the tumor reached a volume of 2000 mm$^3$. The adapted survival curves for tumors to reach this volume show (FIG. 4A) that at day 120, no tumor larger than 2000 mm$^3$ can be observed in the combined antibody group, whereas four out of six mice from both groups treated with a single mAb had tumors reaching that volume (P=0.0072). Furthermore, a complete tumor remission can be observed only in the combined mAb therapy group. Interestingly, in a separate experiment, treatment of MiaPaCa-2 xenografts of similar size (65±6 mm3) with only 25 µg of each antibody in combination has an efficient anti-tumor effect, whereas single mAb injections have almost no growth inhibition effect, confirming, for this tumor also, the important role of the attack by two mAbs directed against different HER receptors. To verify whether the therapeutic advantage of the combined action of the two anti-HER receptor mAbs observed against the two pancreatic carcinoma cell lines can also function on another type of carcinoma, the same comparison between single and combined mAb injections is tested on the reference ovarian carcinoma line SK-OV-3, known to overexpress both EGF and HER-2 receptors. The therapy consisting of 200 µg of either anti-EGFR or anti-HER-2 mAb, or the two mAbs in combination, was initiated in four groups of six mice (including an untreated control) when the SK-OV-3 xenograft had a median volume of 42±4 mm$^3$. As expected, in view of the overexpression of both HER receptors on these tumor cells, a therapeutic activity of each single mAb can be observed with 1 and 2 complete remissions in the group of mice injected with anti-EGFR and anti-HER2, respectively. However, the injection of both mAbs give a clearly superior tumor growth inhibition in all mice, including three complete remissions. The results of the adapted survival curve for the tumor to reach a volume of 1000 mm$^3$ (FIG. 4B) show that the tumors of all six mice treated with the mAb combination did not reach 1000 mm$^3$ during the period of observation of 120 days, while the delay for 50% of the mice to reach this tumor volume was 69 days and 85 days for the group of mice treated with anti-EGFR and HER2, respectively (P=0.0001). These results confirm the therapeutic synergism of the two anti-HER mice mAbs against a human ovarian carcinoma xenograft and suggests that the combined injection of these two mAbs could be useful in the treatment of many types of carcinomas expressing EGF and HER2 receptors.

Inhibition of Receptor Auto-Phosphorylation.

Figure 5:
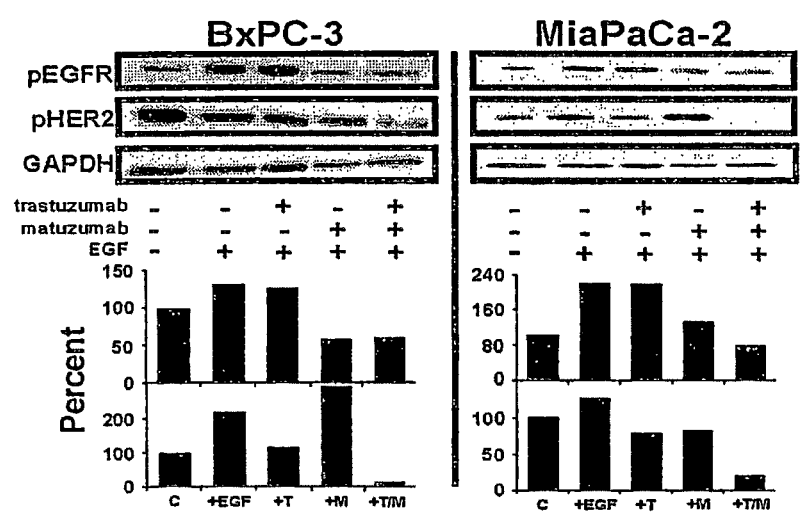

The ability of matuzumab or trastuzumab used alone or in combination to inhibit the tyrosine kinase activity of EGFR and HER2 on BxPC-3 and MiaPaCa-2 cells in vitro, can be assessed by western blot with quantification of the phosphorylated proteins by densitometry and analysis using the NIH imager 6.3 (FIG. 5). Analysis on the two pancreatic carcinoma cell lines are compared after a 48-h incubation with the two mAbs, either alone or in combination, followed by a 10-min activation with EGF. It should be noted first, that both cell lines show a relatively high phosphorylation base line for the EGFR and the HER2 receptor. As expected, treatment with exogenous EGF induces a high level of tyrosine autophosphorylation of EGFR and HER2 in both cell lines. Interestingly, incubation with the mAbs in combination results in a much higher inhibition of phosphorylation of HER2 in both cell lines than that obtained with anti-HER2 mAb alone. For EGFR, the phosphorylation inhibition by the two mAbs is less contrasted; it is almost identical and only slightly superior to that obtained with the anti-EGFR mAb alone on the MiaPaCa-2 and BxPC-3 cells, respectively. These results, as well as more extensive in vitro studies from the literature (22-24), may explain the striking in vivo therapeutic synergism of the two anti-HER receptor Mabs against human carcinoma xenografts described here.

Despite a high EGFR expression in the pancreatic BxPC-3 cell line, matuzumab (EMD72000) is not or only little effective on tumor growth inhibition used alone at a dose of 50 or 200 µg/injection, confirming the absence of correlation between EGFR expression and curative efficacy of anti-EGFR antibodies. This can be illustrated with a secondin vivo pancreatic cancer model (MiaPaca) where mice are treated with 50 µg/injection of EMD72000 twice a week for four weeks. The anti-tumor activity of the combination, however, is much stronger than the negligible antitumor activity of the antibodies used as single components alone. With regard to decreased tumor volume and in vitro viability studies, the effect of the combined antibodies is clearly synergistic in the BxPC-3 model and not a mere additive effect calculated from the efficacies of the single components. This effect is particularly striking during the four-week treatment period, where no tumor progression can be observed in the combined treatment group. Similar efficacy of this treatment can be observed on both small and large pancreatic tumors.

The principle of combined treatment with monoclonal antibodies, with different specificities to antigen structures on the same or different receptors is described here exemplarily for treatment of EGFR and HER 2 positive pancreatic tumor. However, this principle is not limited to pancreatic cancer and can be adapted for use with any other cancer showing the same or a similar receptor expression profile. If not otherwise pointed out the terms and phrases used in this invention have the meanings and definitions as given below. Moreover, these definitions and meanings describe the invention in more detail, preferred embodiments included.

By definition, the term "overexpressed" means according to the invention, that the corresponding receptor is expressed on the surface of the tumor cells with a higher, preferably significantly higher rate and/or amount than on the surface of normal, non-tumor cells preferably deriving from the same tissue.

Usually, EGFR and HER2 are expressed in very low up to low rates on many normal tissue cells, depending on the specific tissue and specimen. In or on tumor tissue these rates are, as a rule, significantly higher, especially with regard to EGFR. With respect to breast cancer, for example, HER2 is significantly overexpressed in at least 30% of the patients and is expressed with a higher level than EGFR. In pancreatic cancer the situation is, as a rule, vice versa. In many cases the situation seems also to be dependent on the genetic predisposition of the individual to be treated. Thus, the terms "moderate expression", "significant expression", etc. are relative terms and must be seen in context of the specific situation. However, in general according to this invention, the term "low expression" means, if not otherwise specified, not "overexpressed" in the sense as indicated above. The term "moderate expression" or "significant" expression means, as not otherwise indicated, "overexpressed" in a lower/moderate or significant/higher rate. "Significant" means in this context that the corresponding tumor cells express the receptor in an amount which is measurably higher than normal non-tumor cells of a specific individual do.

A "receptor" or "receptor molecule" is a soluble or membrane bound/associated protein or glycoprotein comprising one or more domains to which a ligand binds to form a receptor-ligand complex. By binding the ligand, which may be an agonist or an antagonist the receptor is activated or inactivated and may initiate or block pathway signaling.

An "ErbB receptor" is a receptor protein tyrosine kinase which belongs, as already specified above, to the ErbB receptor family and includes EGFR/HER1 (ErbB1), HER2 (ErbB2), ErbB3 and ErbB4 receptors and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably the ErbB receptor is native sequence human ErbB receptor. The expressions "ErbB1" and "HER1" and "EGFR" are used interchangeably herein and refer to human HER1 protein. The expressions "ErbB2" and "HER2" are used interchangeably herein and refer to human HER2 protein. ErbB1 receptors (EGFR) are preferred according to this invention.

The term "ErbB receptor antagonist/inhibitor" refers to a biologically effective molecule, which binds and blocks or inhibits the ErbB receptor. Thus, by blocking the receptor the antagonist prevents binding of the ErbB ligand (agonist) and activation of the agonist/ligand receptor complex. ErbB antagonists may be directed to HER1 (ErbB1, EGFR), HER2 (ErbB2) and ErbB3 and ErbB4.

Preferred antibodies of the invention are anti-Her1 and anti-Her2 antibodies. Preferred anti-Her1 antibodies are MAb 425, preferably humanized MAb 425 (hMAb 425, matuzumab, EMD 72000, U.S. Pat. No. 5,558,864; EP 0531 472) and chimeric MAb 225 (cetuximab, ERBITUX®). Most preferred anti-HER2 antibody is HERCEPTIN® commercialized by Genentech/Roche.

The term "tyrosine kinase antagonist/inhibitor" refers according to this invention to natural or synthetic agents that are enabled to inhibit or block tyrosine kinases, receptor tyrosine kinases included. Thus, the term includes per se ErbB receptor antagonists/inhibitors as defined above. With exception of the anti-ErbB receptor antibodies mentioned above and below, more preferable tyrosine kinase antagonist agents under this definition are chemical compounds which have shown efficacy in mono-drug therapy for breast and prostate cancer. One of the most promising anti-cancer agents in this context is gefitinib (IRESSA®, Astra Zeneca), which is reported to possess outstanding therapeutic efficacy and excellent tolerability in patients with non-small cell lung cancer (NSCLC) as well as advanced head and neck cancer. Preferably, the dosage of the chemical tyrosine kinase inhibitors as defined above is from 1 pg/kg to 1 g/kg of body weight per day. More preferably, the dosage of tyrosine kinase inhibitors is from 0.01 mg/kg to 100 mg/kg of body weight per day.

The invention relates not only to the anti-HER/ErbB antibodies as mentioned but also to their biologically active fragments and to immunoconjugates as specified below, especially immunocytokines.

Depending on the amino acid sequence of their constant regions, intact antibodies can be assigned to different "antibody (immunoglobulin) classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$ and $\mu$ respectively. Preferred major class for antibodies according to the invention is IgG, in more detail IgG1 and IgG2.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well known recombinant DNA methods (see, e.g., U.S. Pat. No. 4,816,567). Monoclonal antibodies may also be isolated from phage antibody libraries using the techniques described in Clackson et al., Nature, 352:624-628 (1991) and Marks et al., J. Mol. Biol., 222:58, 1-597 (1991), for example.

The term "chimeric antibody" means antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g.: U.S. Pat. No. 4,816,567; Morrison et al., Proc. Nat. Acad. Sci. USA, 81:6851-6855 (1984)). Methods for making chimeric and humanized antibodies are also known in the art. For example, methods for making chimeric antibodies include those described in patents by Boss (Celltech) and by Cabilly (Genentech) (U.S. Pat. No. 4,816,397; U.S. Pat. No. 4,816,567).

"Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or non human primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

"Antibody fragments" comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3. Preferably, the intact antibody has one or more effector functions. Papain digestion of antibodies produces two identical antigen-binding fragments, called "Fab" fragments, each comprising a single antigen-binding site and a CL and a CH1 region, and a residual "Fc" fragment, whose name reflects its ability to crystallize readily. The "Fc" region of the antibodies comprises, as a rule, a CH2, CH3 and the hinge region of an IgG1 or IgG2 antibody major class. The hinge region is a group of about 15 amino acid residues which combine the CH1 region with the CH2-CH3 region. Pepsin treatment yields an "F(ab')2" fragment that has two antigen-binding sites and is still capable of cross-linking antigen. "FV" is the minimum antibody fragment which contains a complete antigen-recognition and antigen-binding site. This region consists of a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The "Fab" fragment also contains the constant domain of the light chain and the first constant domain (CH1) of the heavy chain and has one antigen-binding site only. "Fab'" fragments differ from Fab fragments by the addition of a few residues at the carboxy terminus of the heavy chain CH1 domain including one or more cysteines from the antibody hinge region. F(ab')2 antibody fragments originally were produced as pairs of Fab' fragments which have hinge cysteines between them. Other chemical couplings of antibody fragments are also known (see e.g. Hermanson, Bioconjugate Techniques, Academic Press, 1996; U.S. Pat. No. 4,342,566). "Single-chain Fv" or "scFv" antibody fragments comprise the V, and V, domains of antibody, wherein these domains are present in a Single polypeptide chain. Preferably, the Fv polypeptide further comprises a polypeptide linker between the VH and VL domains which enables the scFv to form the desired structure for antigen binding. Single-chain FV antibodies are known, for example, from Plûckthun (The Pharmacology of Monoclonal Antibodies, Vol. 113, Rosenburg and Moore eds., Springer-Verlag, New York, pp. 269-315 (1994)), WO93/16185; U.S. Pat. No. 5,571,894; U.S. Pat. No. 5,587,458; Huston et al. (1988, Proc. Natl. Acad. Sci. 85, 5879) or Skerra and Plueckthun (1988, Science 240, 1038).

"Bispecific antibodies" (BAbs) are single, divalent antibodies (or immunotherapeutically effective fragments thereof) which have two differently specific antigen binding sites. According to this invention BAbs are characterized as BAb <MAb 1, MAb 2>, wherein <MAb 1> and <MAb 2> designates the antigen-binding sites deriving from MAb 1 and MAb 2. For example the first antigen binding site is directed to an angiogenesis receptor (e.g. integrin or VEGF receptor), whereas the second antigen binding site is directed to an ErbB receptor (e.g. EGFR or HER2). Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. Further methods are described in WO 91/00360, WO 92/05793 and WO 96/04305. Bispecific antibodies can also be prepared from single chain antibodies (see e.g., Huston et al. (1988) Proc. Natl. Acad. Sci. 85, 5879; Skerra and Plueckthun (1988) Science 240, 1038). These are analogues of antibody variable regions produced as a single polypeptide chain. To form the bispecific binding agent, the single chain antibodies may be coupled together chemically or by genetic engineering methods known in the art. It is also possible to produce bispecific antibodies according to this invention by using leucine zipper sequences. The sequences employed are derived from the leucine zipper regions of the transcription factors Fos and Jun (Landschulz et al., 1988, Science 240, 1759; for review, see Maniatis and Abel, 1989, Nature 341, 24). Leucine zippers are specific amino acid sequences about 20-40 residues long with leucine typically occurring at every seventh residue. Such zipper sequences form amphipathic α-helices, with the leucine residues lined up on the hydrophobic side for dimer formation. Peptides corresponding to the leucine zippers of the Fos and Jun proteins form heterodimers preferentially (O'Shea et al., 1989, Science 245, 646). Zipper containing bispecific antibodies and methods for making them are also disclosed in WO 92/10209 and WO 93/11162.

The term "immunoconjugate" refers to a fusion protein and means an antibody or immunoglobulin, respectively, or a immunologically effective fragment thereof, which is fused by covalent linkage to a non-immunologically effective molecule. Preferably this fusion partner is a peptide or a protein, which may be glycosylated. Said non-antibody molecule can be linked to the C-terminal of the constant heavy chains of the antibody or to the N-terminals of the variable light and/or heavy chains. The fusion partners can be linked via a linker molecule, which is, as a rule, a 3-15 amino acid residues containing peptide. Immunoconjugates according to this invention are fusion proteins consisting of an immunoglobulin or immunotherapeutically effective fragment thereof, directed to an ErbB receptor, and preferably a cytokine, such as TNFα, IFNγ or IL-2, or another toxic agent. Preferably, these peptide- or protein-based molecules are linked with their N-terminal to the C-terminal of said immunoglobulin, which is the Fc portion thereof. The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; mouse gonadotropin-associated peptide; inhibin; activin; vascular endothelial growth factor (VEGF); integrin; thrombopoietin (TPO); nerve growth factors such as NGFβ; platelet-growth factor; transforming growth factors (TGFs) such as TGFα and TGFβ; erythropoietin (EPO); interferons such as IFNα, IFNβ, and IFNγ; colony stimulating factors such as M-CSF, GM-CSF and G-CSF; interleukins such as IL-1, IL-la, IL-2, IL-3, IL-4, IL-5, IL-6, IL-7, IL-8, IL-9, IL-10, IL-11, IL-12; and TNF-α or TNF-β. Preferred cytokines according to the invention are interferons, TNFα and IL-2.

The term "immunotherapeutically or immunobiologically effective" refers to biological molecules which cause an immune response in a mammal. More specifically, the term refers to molecules which may recognize and bind an antigen. Typically, antibodies, antibody fragments and antibody fusion proteins comprising their antigen binding sites (complementary determining regions, CDRs) are immunotherapeutically effective.

The therapeutic approach of this invention includes as a specific embodiment the administration of further therapeutically effective agents, which support the desired effect, e.g. tumor toxicity or cytostatic efficacy, or diminish or prevent undesired side effects. Thus the invention includes the combination of such agents with the pharmaceutical composition defined and claimed above and below, wherein said agents may be other ErbB receptor antagonists, VEGF receptor antagonists, cytokines, cytokine-immunoconjugates, anti-angiogenic agents, anti-hormonal agents, or cytotoxic agents in general. It is also an object of this invention to combine the compositions as defined herein with radiotherapy according to known methods.

The term "cytotoxic agent" as used in this context is defined very broadly and refers to a substance that inhibits or prevents the function of cells and/or causes destruction of cells (cell death), and/or exerts anti-neoplastic/anti-proliferative effects, for example, prevents directly or indirectly the development, maturation or spread of neoplastic tumor cells. The term includes expressively also such agents that cause a cytostatic effect only and not a mere cytotoxic effect.

The term "chemotherapeutic agent" is a subset of the term "cytotoxic agent" and means specifically chemical agents that exert anti-neoplastic effects, preferably directly on the tumor cell, and less indirectly through mechanisms such as biological response modification. Suitable chemotherapeutic agents according to the invention are preferably natural or synthetic chemical compounds. There are large numbers of anti-neoplastic chemical agents available in commercial use, in clinical evaluation and in pre-clinical development, which could be included in the present invention for treatment of tumors/neoplasia by combination therapy with the receptor antagonists as claimed and described in this invention. The term includes especially agents as specified below, as well as other ErbB antagonists (such as anti-ErbB antibodies), anti-angiogenic agents, tyrosine kinase inhibitors, protein kinase A inhibitors, members of the cytokine family, radioactive isotopes, and toxins such as enzymatically active toxins of bacterial, fungal, plant or animal origin. Preferred chemotherapeutic agents are amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), gefitinib (Iressa), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention are cisplatin, gemcitabine, doxorubicin, paclitaxel (taxol) and bleomycin.

The terms "cancer" and "tumor" refer to or describe the physiological condition in mammals that is typically characterized by unregulated cell growth. By means of the pharmaceutical compositions according of the present invention tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

Tumors which can be preferably be treated with the antibody molecules according to the invention are solid tumors or tumor metastases that express ErbB receptors, especially ErbB1 receptors, in high amounts, such as breast cancer, prostate cancer head and neck cancer, SCLC, pancreas cancer but with respect to ErbB2 (HER2) receptors also in lower amounts.

The term "biologically/functionally effective" or "therapeutically effective (amount)" refers to a drug/molecule which causes a biological function or a change of a biological function in vivo or in vitro, and which is effective in a specific amount to treat a disease or disorder in a mammal, preferably in a human.

"Radiotherapy": According to the invention the tumors can additionally be treated with radiation or radiopharmaceuticals. The source of radiation can be either external or internal to the patient being treated. When the source is external to the patient, the therapy is known as external beam radiation therapy (EBRT). When the source of radiation is internal to the patient, the treatment is called brachytherapy (BT). Some typical radioactive atoms that have been used include radium, cesium-137, and iridium-192, americium-241 and gold-198, Cobalt-57; Copper-67; Technetium-99; Iodide-123; Iodide-131; and Indium-111. It is also possible to label the agents according to the invention with radioactive isotopes. Today radiation therapy is the standard treatment to control unresectable or inoperable tumors and/or tumor metastases. Improved results have been seen when radiation therapy has been combined with chemotherapy.

"Pharmaceutical treatment": The agents of this invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, the agents of this invention can be administered intraocularly, intravenously, intraperitoneally, intramuscularly, subcutaneously, intracavity, transdermally, by orthotopic injection and infusion, and can also be delivered by peristaltic means. Therapeutic compositions of the present invention contain a physiologically tolerable carrier together with the relevant agent as described herein, dissolved or dispersed therein as an active ingredient.

As used herein, the term "pharmaceutically acceptable" refers to compositions, carriers, diluents and reagents which represent materials that are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions.

Typically, a therapeutically effective amount of an immunotherapeutic agent, for example, in the form of an ErbB (ErbB1, ErbB2) receptor blocking antibody or a corresponding antibody conjugate is an amount such that, when administered in physiologically tolerable composition, is sufficient to achieve a plasma concentration of from about 0.01 microgram (µg) per milliliter (ml) to about 100 µg/ml, preferably from about 1 µg/ml to about 5 µg/ml and usually about 5 µg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily for one or several days. Where the immunotherapeutic agent is in the form of a fragment of a monoclonal antibody or a conjugate, the amount can readily be adjusted based on the mass of the fragment/conjugate relative to the mass of the whole antibody. A preferred plasma concentration in molarity is from about 2 micromolar (µM) to about 5 millimolar (mM) and preferably, about 100 µM to 1 mM antibody antagonist.

The typical dosage of an active agent, which is a preferably a chemical cytotoxic or chemotherapeutic agent according to the invention (neither an immunotherapeutic agent nor a non-immunotherapeutic peptide/protein) is 10 mg to 1000 mg, preferably about 20 to 200 mg, and more preferably 50 to 100 mg per kilogram body weight per day.

The pharmaceutical compositions of the invention can comprise phrase encompasses treatment of a subject with agents that reduce or avoid side effects associated with the combination therapy of the present invention ("adjunctive therapy"), including, but not limited to, those agents, for example, that reduce the toxic effect of anticancer drugs, e.g., bone resorption inhibitors, cardioprotective agents. Said adjunctive agents prevent or reduce the incidence of nausea and vomiting associated with chemotherapy, radiotherapy or operation, or reduce the incidence of infection associated with the administration of myelosuppressive anti-cancer drugs. Adjunctive agents are well known in the art. The immunotherapeutic agents according to the invention can additionally administered with adjuvants like BCG and immune system stimulators. Furthermore, the compositions may include immunotherapeutic agents or chemotherapeutic agents which contain cytotoxic effective radio-labeled isotopes, or other cytotoxic agents, such as a cytotoxic peptides (e.g. cytokines) or cytotoxic drugs and the like.

Source of Cell Lines.

Cell Lines and Culture Conditions. Human pancreatic (BxPC-3 and MiaPaCa-2), ovarian (SK-OV-3), and vulvar epidermoid (A-431) carcinoma cell lines were obtained from the American Type Culture Collection (ATCC; Rockville, Md., USA). The BxPC-3 cell line was cultured in RPMI-1640 medium (Gibco, Paisley, UK); the MiaPaCa-2, SK-OV-3, and A-431 cell lines were cultured in DMEM medium (Gibco). The culture media were supplemented as recommended by ATCC.

SHORT DESCRIPTION OF THE FIGURES

FIG. 1 Immunocytochemical and flow cytometry analyses of EGFR and HER2 expression on the two pancreatic carcinoma cell lines, BxPC-3 and MiaPaCa-2, and on the two reference cell lines, A-431 and SK-OV-3 used as positive controls for EGFR and HER2, respectively. NC (negative controls): tissues incubated only with the immunoperoxidase conjugate. In flow cytometry analyses, black and gray peaks depict cell surface staining with the anti-EGFR and the anti-HER2 antibodies, respectively. The white peaks represent controls, obtained with cells incubated only with the FITC-labeled second antibody.

Figure 2:
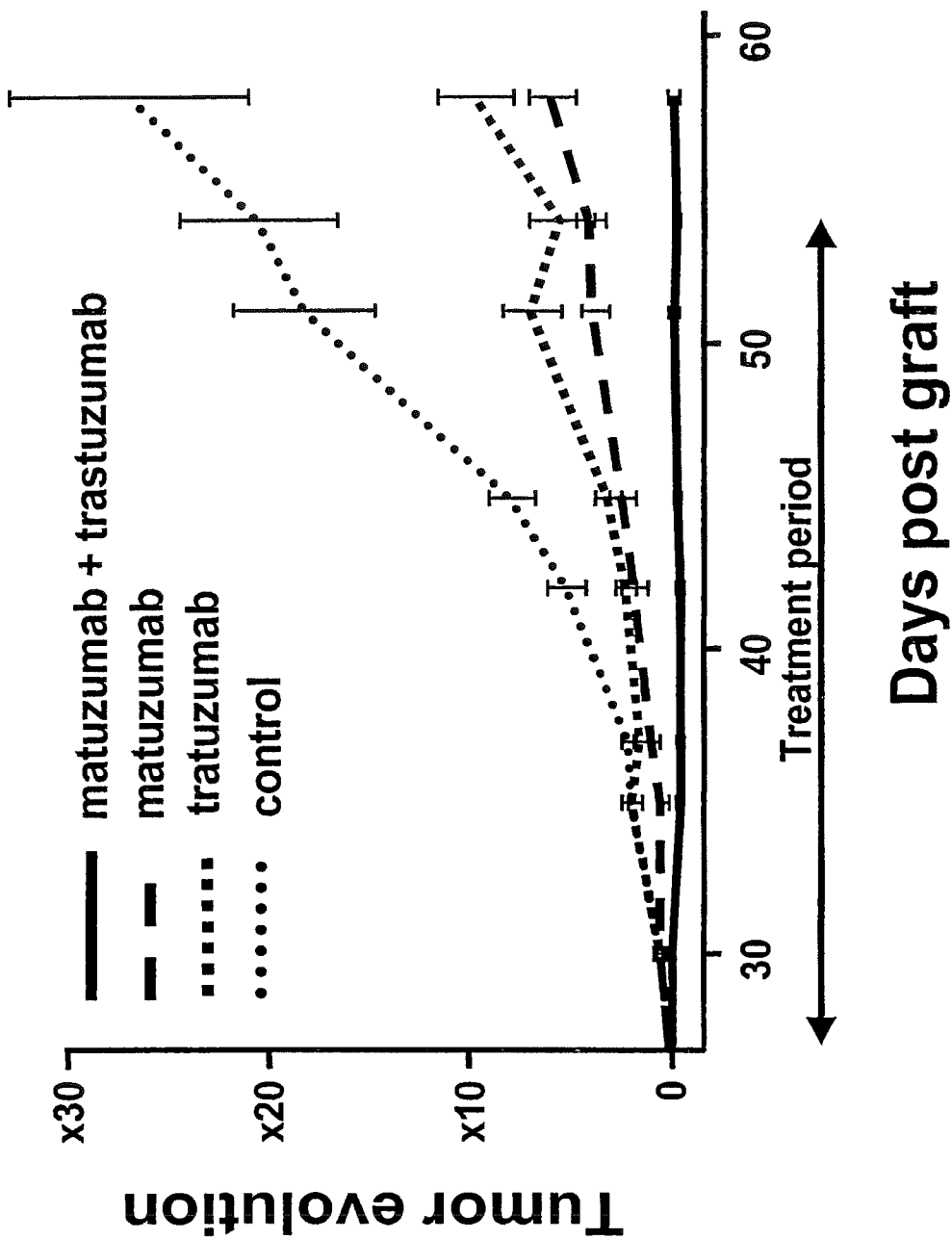

FIG. 2 Effects of trastuzumab and matuzumab alone or in combination on the growth of small size BxPC-3 xenografts in nude mice (experiment S). Mean pretreatment tumor volumes were 77±49 mm$^3$. Mice (eight per group) received i.p. injections of 50 ng of each mAb twice a week for four weeks. Results are expressed as tumor progression: [(final volume)−(initial volume)]/(initial volume). C: control; T: trastuzumab; M: matuzumab; T+M: trastuzumab+matuzumab.

Figure 3B:
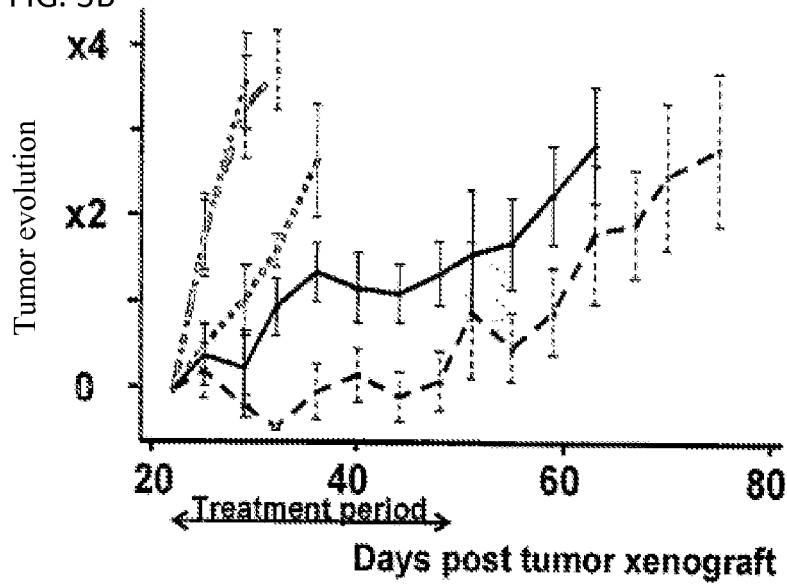

FIGS. 3A-3B Effects of trastuzumab and matuzumab alone or in combination on the growth of large-size BxPC-3 xenografts in nude mice (experiment L). Mean pretreatment tumor volumes were 502±205 mm$^3$. Mice (five per group) received i.p. injections of 50 ng or 200 ng of each mAb twice a week for four weeks. FIG. 3A, Kaplan-Meier survival curves obtained as a function of time adapted for primary tumor to reach a volume of 1500 mm$^3$. C: control; T: trastuzumab (200 µg per injection); M: matuzumab (200 µg per injection); T+M: trastuzumab+matuzumab (50 or 200 µg of each mAb per injection). FIG. 3B, results from the same experiments, expressed as tumor progression curves. Double head arrows indicate the treatment period.

Figure 4A:
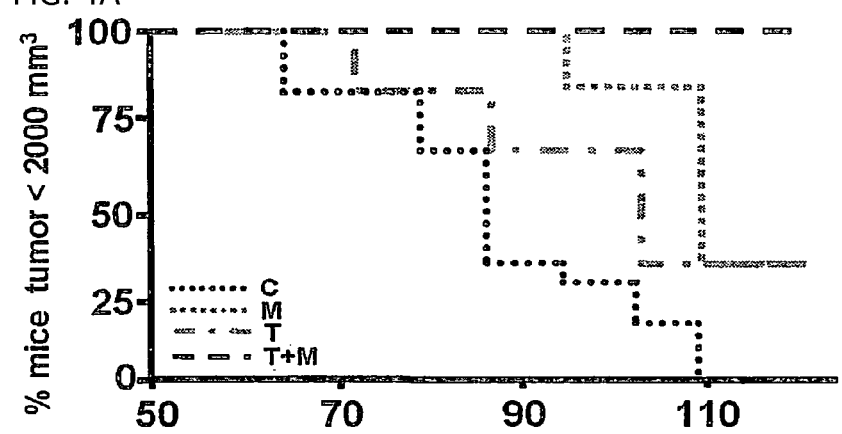
Figure 4B:
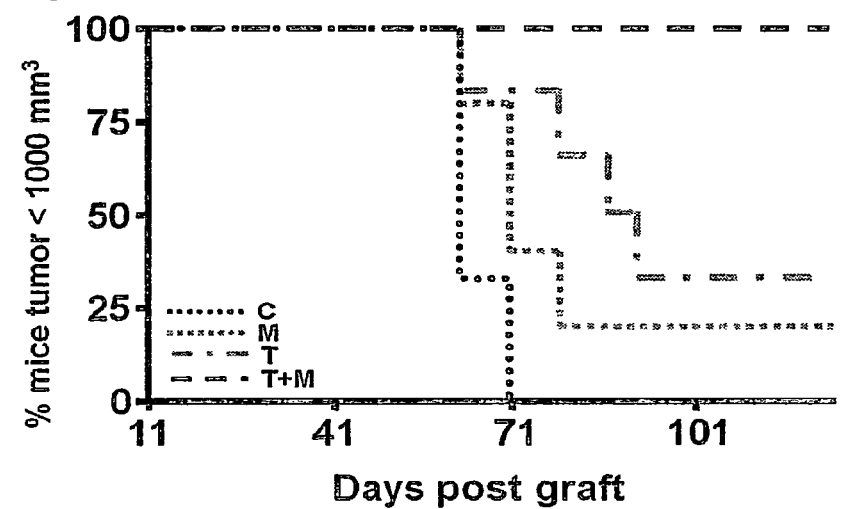

FIG. 4A, Effects of trastuzumab and matuzumab alone or in combination on the growth of MiaPaCa-2 xenografts in nude mice. Mean (six per group) pretreatment tumor volumes were 64±5 mm$^3$. Mice received i.p. injections of 50 µg of each mAb twice a week for four weeks from day 15 to 43. A Kaplan-Meier survival curves obtained as a function of time adapted for primary tumor to reach a volume of 2000 mm$^3$. C: control; T: trastuzumab; M: matuzumab; T+M: trastuzumab+matuzumab. FIG. 4B, Effects of trastuzumab and matuzumab alone or in combination on the growth of SK-OV-3 xenografts in nude mice. Mean (six per group) pretreatment tumor volumes were 42±4 mm3. Mice received i.p. injections of 200 µg of each mAb twice a week for four weeks from day 11 to 40. A Kaplan-Meier survival curves for primary tumor to reach a volume of 1000 mm$^3$. C: control; T: trastuzumab; M: matuzumab; T+M: trastuzumab+matuzumab.

FIG. 5 In vitro effect of trastuzumab and matuzumab alone or in combination on EGFR and HER2 phosphorylation on BxPC-3 and MiaPaCa-2 cell lines. Cells were incubated with 10 ng/ml of each mAb for 48 h followed by 10 min with 100 ng/ml of EGF or no EGF. Upper panel: western blot analysis, GAPDH=loading control. Lower panel: quantification of receptor phosphorylation, expressed in percent of control and plotted as a bar graph, show the inhibition induced by the indicated treatment conditions. C: control; T: trastuzumab; M: matuzumab; T/M: trastuzumab+matuzumab.

Figures 6A, 6B:
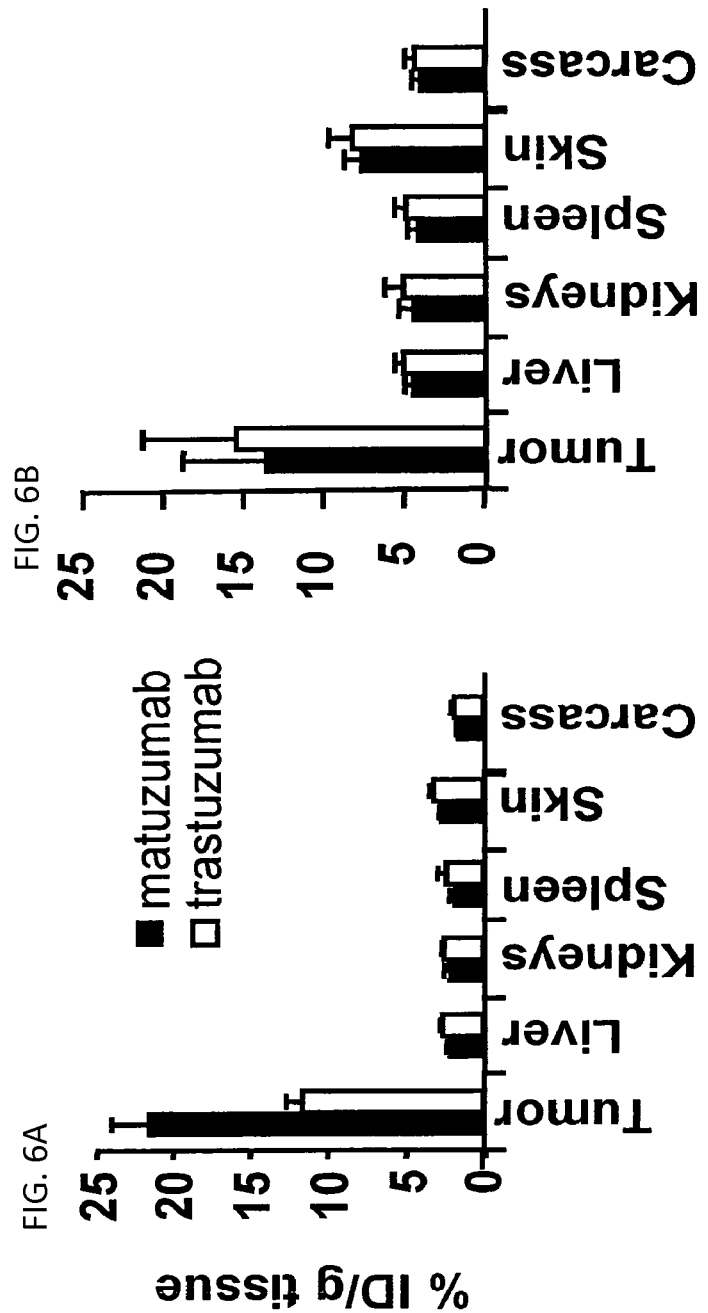

FIGS. 6A-6B Tumor localization and biodistribution of radiolabeled matuzumab and trastuzumab antibodies in athymic NMRI mice bearing human pancreatic carcinoma BxPC-3 FIG. 6A or MiaPaCa-2 FIG. 6B xenografts. Mice received an i.v. co-injection of 125I-matuzumab and 131I-trastuzumab. Mice were sacrificed forty-eight hours post-injection. The tumor, and all normal organs were weighed, and the differential radioactivity was measured in a dual channel scintillation counter. The results are expressed as the percentage of the injected dose of radioactivity present per gram of tissue (% ID/g).

Figure 7:
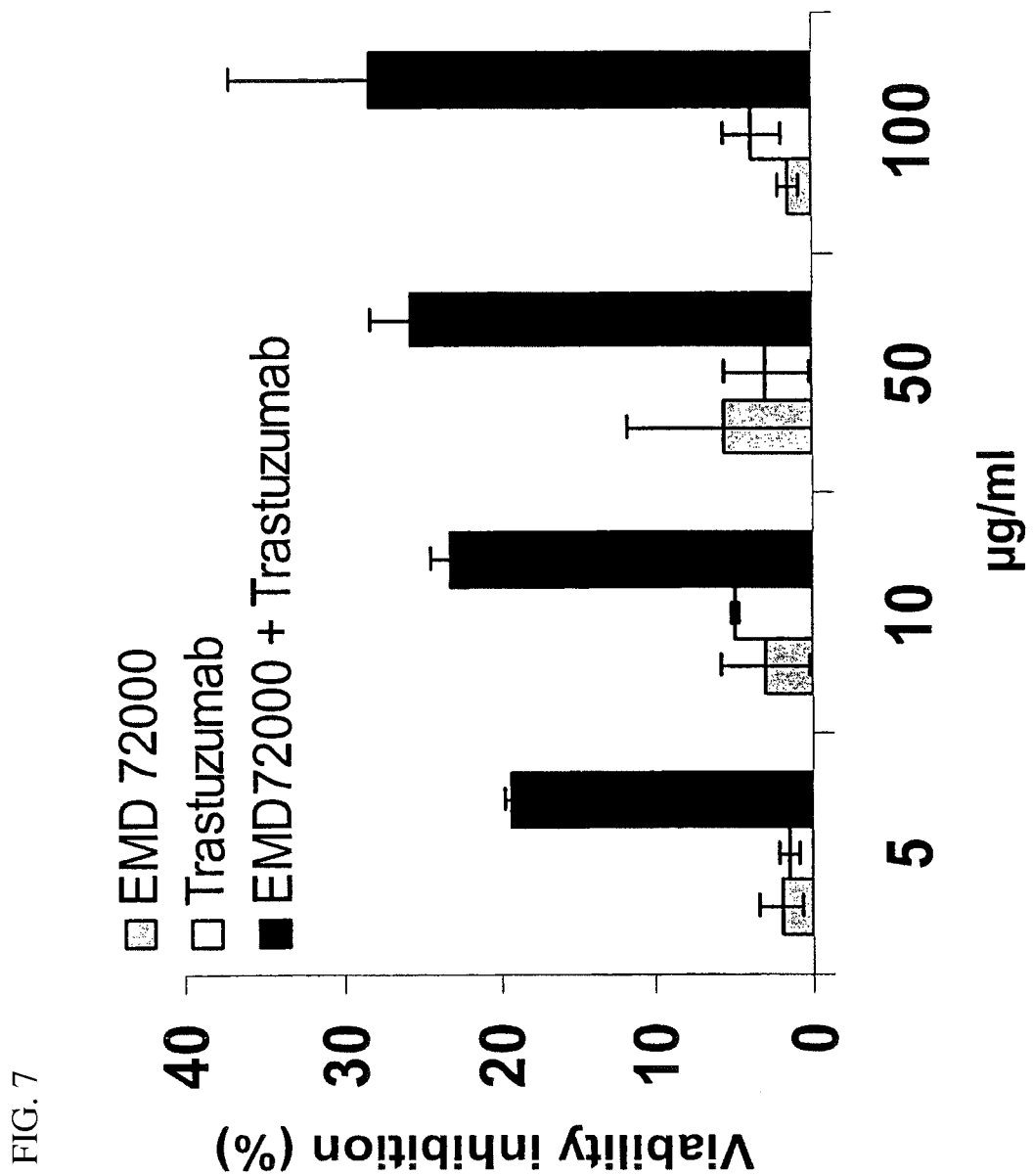

FIG. 7 In vitro growth inhibition of BxPC-3 cells treated with trastuzumab and matuzumab alone or in combination. BxPC-3 cells were seeded at 10,000 cells/well in a 96-well plate and allowed to adhere overnight. The next day, cells were treated with trastuzumab and matuzumab alone or in combination at a fixed 1:1 ratio. After five days, the MTS assay was performed as described in Materials and Methods. Each value represents the mean±SEM (n=6).

EXAMPLES

Example 1

In Vivo Tumor Growth Inhibition Study

All in vivo experiments were performed in compliance with the French guidelines for experimental animal studies (Agreement No. B34-172-27). Nude mice, 6-8-week-old female athymic NMRI mice and BALB/c athymic mice were purchased from Janvier, Le Genest (St Isle, France) and Charles Rivers Laboratories (L'Arbresle, France), respectively. BxPC-3 (3.5×10$^6$), MiaPaCa-2 (5×106) and SK-OV-3 (5×10$^6$) cells were injected subcutaneously (s.c.) in to the right flank of athymic NMRI (BxPC-3 model) and BALB/c (MiaPaCa-2 and SK-OV-3) nude mice. MiaPaCa-2 cells were suspending in 50% culture medium and 50% Matrigel (BD biosciences, Le Pont De claix, France). Tumor-bearing mice were randomized in the different treatment groups when the tumors reached an approximate volume indicated in each experiment. For the BxPC-3 model, effects of antibody treatments were studied on small tumor (experiment S) and on large tumor (experiment L). The mice were treated by intraperitonal injections (i.p.) with 0.9% NaCl, trastuzumab, matuzumab, or both mAbs at a ratio of 1:1. The amounts of each injected mAb were 50 ng or 200 ng per injection depending on the experiment, twice a week for four weeks consecutively. Tumor dimensions were measured twice weekly with a caliper and the volumes calculated by the formula: D1×D2×D3/2. Tumor progression was calculated using the formula: [(final volume)–(initial volume)]/(initial volume). The results were also expressed by an adapted Kaplan-Meier survival curve, using the time taken for the tumor to reach a determined volume of 1000 mm$^3$ for SK-OV-3, 1500 mm3 for BxPC-3 and 2000 mm$^3$ for MiaPaCa-2 xenografts, depending on the rapidity of growth of the tumors. A median delay was defined as the time at which 50% of the mice had a tumor reaching the determined volume. For experiment S in the BxPC-3 model, an increment factor during the treatment period was calculated by dividing the tumor volume at the end of treatment (day 55) by that at the beginning of the treatment (day 27).

Example 2

Immunocytochemical Analyses

Expression of receptors was analyzed in paraffin-embedded cells fixed in AFA (alcohol formol acetic acid). Analysis of EGFR expression was performed by using the EGFR pharmDx kit (DakoCytomation, Carpinteria, Calif., USA) according to the manufacturer's recommendations. Diaminobenzidine (Dakocytomation) was used as the chromogen, and the sections were lightly counterstained with hematoxylin. The primary antibody used for the detection of HER2 was a rabbit polyclonal antibody (Dakocytomation).

Example 3

Immunoblotting Analysis

BxPC-3 and MiaPaCa-2 cells, plated at 106 cells for 24 h in Petri dishes were starved for two days in a medium without growth factors (SM medium) and treated with 10 Ng/ml of trastuzumab, matuzumab or both antibodies at a fixed 1:1 ratio (or controls without antibody). After a 48-h incubation, cells were incubated for 10 min in the SM medium with or without 100 ng/ml of EGF, washed twice, and lysed with buffer (CliniSciences SA, Montrouge, France) containing 100 NM PMSF, 100 mM sodium fluorure, 1 mM sodium orthovanate, and one complete protease inhibitor mixture tablet (Sigma, St Louis, Mo.). After electrophoresis on 8% SDS-PAGE under non-reducing conditions, the proteins were transferred to a polyvinylidene difluoride membranes (Millipore Co., Bedford, Mass.) which were saturated in PBS containing 0.1% Tween 20 and 5% nonfat dry milk and then incubated with the antibodies against the phosphorylated forms of EGFR and HER2, obtained from Cell Signaling Technology (Beverly, Mass.). To ensure equal loading, immunoblots were also probed with anti-GAPDH (glyceraldehydes-3-phosphate deshydrogenase) antibody (Chemicon international, Australia).

Example 4

Cell Viability Assay

The effect of trastuzumab and/or EMD72000 on cell viability was evaluated using a tetrazolium salt (MTS) and an electron coupling reagent (PMSF) assay. Briefly, BxPC-3 cells were plated in 96-well microtiter plates at 10,000 cells/well in 100 HI of medium. After 24 h, the cells were treated with antibodies at concentrations ranging from 5 to 100 Hg/ml. After incubation of 96 h, cells were exposed to MTS (3-(4,5-dimethylthiazol-2-yl)-5-(3-carboxymethoxyphenyl)-2-(4-sulfophenyl)-2H-tetrazolium) reagent and incubated at 37° C. for 2 h. Absorbance was measured at 490 nm, and the percent inhibition of viability was calculated as the percent of proliferating cells compared with untreated cultures. All experiments were performed in triplicate.

The invention claimed is:

1. A method for treating pancreatic cancer in an individual, wherein said pancreatic cancer in said individual overexpresses EGFR and does not or not significantly expresses HER2, the method comprising administering to the individual an anti-HER2 antibody and an anti-EGFR antibody, said anti-HER2 antibody and said anti-EGFR antibody being both part of the same bispecific antibody, wherein said anti-HER2 antibody is murine, chimeric or humanized mAb 4D5 (trastuzumab) or pertuzumab and said anti-EGFR antibody is murine, chimeric or humanized mAb 425 (matuzumab); chimeric mAb 225 (cetuximab); or panitumumab.

2. The method of claim 1, wherein HER2 is not expressed.

3. The method of claim 1, wherein said antibody is fused at its C-terminus to a biologically effective peptide, polypeptide or protein, optionally via a linker peptide, thus forming an immunoconjugate.

4. The method of claim 3, wherein said immunoconjugate is an immunocytokine.

5. The method of claim 1, wherein said pancreatic cancer in said individual has been determined to overexpress EGFR and to not or not significantly express HER2.

6. The method according to claim 1, wherein EGFR are expressed with a higher rate and/or amount than for normal non-tumor cells.

7. A method for improving the efficacy of the treatment of pancreatic cancer with an anti-HER2 antibody, wherein said pancreatic cancer in said individual overexpresses EGFR and does not or not significantly expresses HER2; the method comprising administering to an individual an anti-HER2 antibody and an anti-EGFR antibody, said anti-HER2 antibody and said anti-EGFR antibody being both part of the same bispecific antibody, wherein said anti-HER2 antibody is murine, chimeric or humanized mAb 4D5 (trastuzumab) or pertuzumab and said anti-EGFR antibody is murine, chimeric or humanized mAb 425 (matuzumab); chimeric mAb 225 (cetuximab); or panitumumab.

8. The method of claim 7, wherein HER2 is not expressed.

9. The method of claim 1, wherein said antibody is immunologically effective fragment.

10. The method of claim 1, wherein additionally a cytotoxic agent is administered to the individual.

11. The method of claim 10, wherein the cytotoxic agent is a chemotherapeutic agent.

12. The method of claim 11, wherein the chemotherapeutic agent is selected from the group consisting of cisplatin, doxorubicin, gemcitabine, docetaxel, paclitaxel, bleomycin and irinotecan.

13. The method of claim 10, wherein the cytotoxic agent is a VEGF receptor inhibitor, a small molecule tyrosine kinase inhibitor, an anti-angiogenic agent, or a cytokine.

14. The method of claim 7, wherein said cancer in said individual has been determined to overexpress EGFR and to not or not significantly express HER2.

15. The method according to claim 7, wherein EGFR are expressed with a higher rate and/or amount than for normal non-tumor cells.

* * * * *